US012594077B2

(12) United States Patent
Yeung et al.

(10) Patent No.: US 12,594,077 B2
(45) Date of Patent: Apr. 7, 2026

(54) ENDOSCOPIC MAGNETIC ANASTOMOSIS SYSTEM, AND METHODS AND DEVICES FOR FORMING AN ANASTOMOSIS

(71) Applicant: iEMIS (HK) Limited, Kowloon (HK)

(72) Inventors: Chung Kwong Yeung, Hong Kong (CN); Wing Fai Lam, Hong Kong (CN); Yasser Khan Eronico Waqar, Hong Kong (CN); Hon Shing Chan, Hong Kong (CN); Biji Sreedhar, Hong Kong (CN)

(73) Assignee: iEMIS (HK) Limited, Kowloon (HK)

( * ) Notice: Subject to any disclaimer, the term of this patent is extended or adjusted under 35 U.S.C. 154(b) by 289 days.

(21) Appl. No.: 18/015,172

(22) PCT Filed: Jul. 7, 2020

(86) PCT No.: PCT/CN2020/100662
§ 371 (c)(1),
(2) Date: Jan. 9, 2023

(87) PCT Pub. No.: WO2022/006742
PCT Pub. Date: Jan. 13, 2022

(65) Prior Publication Data
US 2023/0248364 A1      Aug. 10, 2023

(51) Int. Cl.
*A61B 17/11* (2006.01)
*A61B 17/00* (2006.01)

(52) U.S. Cl.
CPC .... *A61B 17/1114* (2013.01); *A61B 17/00234* (2013.01); *A61B 2017/00557* (2013.01);
(Continued)

(58) Field of Classification Search
CPC .......... A61B 17/1114; A61B 17/00234; A61B 2017/00557; A61B 2017/00818;
(Continued)

(56) References Cited

U.S. PATENT DOCUMENTS

| | | | |
|---|---|---|---|
| 9,456,820 | B2 | 10/2016 | Gagner et al. |
| 2008/0208224 | A1 | 8/2008 | Surti et al. |
| 2010/0292729 | A1 | 11/2010 | Aguirre et al. |

FOREIGN PATENT DOCUMENTS

| | | |
|---|---|---|
| CN | 104619269 A | 5/2015 |
| CN | 105078534 A | 11/2015 |

OTHER PUBLICATIONS

An International Search Report and the Written Opinion of the International Searching Authority issued on Apr. 6, 2021 in connections with International Application No. PCT/CN2020/100662.

*Primary Examiner* — Richard G Louis

(57) ABSTRACT

An endoscopic anastomosis system (100), devices, and methods. The system (100) includes a first main body (200). The system (100) includes a head assembly (300) secured to the first main body (200). The head assembly (300) includes an opening (318), a first pressure port (332), and a first expandable member (320). The system (100) includes a second main body assembly (400), at least a portion of the second main body assembly (400) moveable through the opening (318) of the head assembly (300). The second main body assembly (400) includes a second expandable member (420) and a second pressure port (422). The system (100) includes a magnetic implant assembly (430) secured to an end of the second main body assembly (400). The magnetic implant assembly (430) includes a magnetic body (432). The magnetic body (432) is formed as a cylindrical body with a central axis. The magnetic body (432) includes a front wall (432a), a rear wall (432b), and a exterior circumferential sidewall (432c) formed around the magnetic body (432). The exterior circumferential sidewall (432c) defines a thickness of the magnetic body (432). The exterior circumferential sidewall (432c) is formed at a first radius from the central axis.

29 Claims, 27 Drawing Sheets

(52) U.S. Cl.
CPC ............... *A61B 2017/00818* (2013.01); *A61B 2017/00876* (2013.01)

(58) Field of Classification Search
CPC .......... A61B 2017/00876; A61B 34/37; A61B 2017/003; A61B 2017/00477; A61B 2017/1139; A61B 2017/22054; A61B 2017/22067; A61B 2017/22069; A61B 2034/301; A61B 2217/002; A61B 2017/306; A61M 2025/0024
See application file for complete search history.

ENDOSCOPIC MAGNETIC ANASTOMOSIS SYSTEM, AND METHODS AND DEVICES FOR FORMING AN ANASTOMOSIS

CROSS-REFERENCE TO RELATED APPLICATIONS

This patent application is a national phase filing under section 371 of PCT/CN2020/100662, filed on Jul. 7, 2020, which is incorporated herein by reference in its entirety.

TECHNICAL FIELD

The present disclosure relates generally to robotic systems, devices, and methods for forming an anastomosis, and more specifically, relates to endoscopic anastomosis systems and devices for an forming anastomosis.

BACKGROUND

Diabetes is emerging as a primary cause of mortality, morbidity, disability, and discrimination in health care, education and employment. The International Diabetes Federation (IDF) estimates nearly half a billion people worldwide are presently living with diabetes. It is estimated that by 2045, the global prevalence will increase by 48%, swelling to an estimated 693 million individuals (aged 18-99 years) afflicted.

The socioeconomic burden associated with these conditions is immense, most of which can be attributed to Diabetes. Hyperglycaemia, a high level of blood glucose, is the hallmark of diabetes. In Type 2 Diabetes (T2DM), hyperglycaemia results from a varying combination of insulin resistance and inadequate insulin production. Chronic hyperglycaemia can cause damage to various organs, leading to the development of disabling and life-threatening complications such as cardiovascular disease, neuropathy, nephropathy, and eye disease leading to retinopathy and blindness. These complications contribute to more frequent hospitalization, increased medical care costs and lower quality of life, and often results in early death.

BRIEF SUMMARY

Present example embodiments relate generally to and/or comprise systems, subsystems, processors, devices, logic, and methods for addressing conventional problems, including those described above.

In an exemplary embodiment, an endoscopic anastomosis system is described. The endoscopic anastomosis system includes a first main body assembly. The first main body assembly is an elongated body having a first end and a second end. At least a portion of the second end of the first main body assembly is controllable to bend in a plurality of directions. The endoscopic anastomosis system includes a head assembly. The head assembly includes a first end and a second end. The head assembly includes a head assembly body and a first expandable member. The head assembly body includes a first region and a second region. The first region includes a first end, a second end, and a midsection between the first and second ends of the first region. The first end of the first region is secured to the second end of the first main body assembly. The second end of the first region includes a first section and a second section. The first section is secured to a first end of a second region of the head assembly. The second section includes a second main body assembly opening. The second region includes the first end and a second end. The second end of the second region includes a first pressure port. The first pressure port is configured to apply a negative pressure. The first expandable member is secured to at least a portion of the midsection of the first region of the head assembly body. The first expandable member is configured to expand radially away from the first region of the head assembly body. The endoscopic anastomosis system includes a second main body assembly. The second main body assembly is an elongated body having a first end and a second end. At least a portion of the second end of the second main body assembly is provided in and moveable through the second main body assembly opening of the second section of the first region of the head assembly body. The second main body assembly includes a second expandable member and a second pressure port. The second expandable member is secured to a portion of the second end of the second main body assembly. The second expandable member is configured to expand radially away from the second main body assembly. The second pressure port is configured to apply a negative pressure. The endoscopic anastomosis system includes a magnetic implant assembly. The magnetic implant assembly includes a magnetic body. The magnetic body is formed as a substantially flat body. The magnetic body includes a front wall, a rear wall opposite to the front wall, and an exterior circumferential sidewall. The front wall has a circular shape with a central axis. The exterior circumferential sidewall is formed around the magnetic body. The exterior circumferential sidewall defines a thickness of the magnetic body. The exterior circumferential sidewall is formed at a first radius from the central axis. The endoscopic anastomosis system includes a securing assembly. The securing assembly is secured to the second end of the second main body assembly. The securing assembly is actuatable between a locked configuration and an unlocked configuration. The locked configuration is a configuration in which the magnetic implant assembly is secured to the securing assembly. The unlocked configuration is a configuration in which the magnetic implant assembly is not secured to the securing assembly.

In another exemplary embodiment, a catheter system for an endoscopic anastomosis system is described. The endoscopic anastomosis system includes a main body and a head assembly. The head assembly is secured to a distal end of the main body. The head assembly includes a head assembly body, a first expandable member, and a first pressure port. The head assembly body includes a first region and a second region. The first region includes a first end and a second end. The first end of the first region includes a first section and a second section. The first section of the first region is secured to the second region. The second section of the first region includes a catheter body opening for at least a portion of the catheter assembly to be provided in and moveable through. The first expandable member is secured to a portion of the first region between the first and second end of the first region. The first pressure port is provided in the second region. The catheter assembly includes a catheter body, a magnetic implant assembly, and a securing assembly. The catheter body is an elongated body. The catheter body includes a first end and a second end. At least a portion of the second end of the catheter body is provided in and moveable through the catheter body opening of the first region of the head assembly body. The catheter body includes a second expandable member and a second pressure port. The second expandable member is secured to a portion of the second end of the catheter body. The second expandable member is configured to expand radially away from the catheter body. The second pressure port is configured to apply a negative pressure. The magnetic implant assembly includes a magnetic body. The magnetic body is formed as a substantially flat body. The magnetic body includes a front wall, a rear wall opposite to the front wall, and an exterior circumferential sidewall. The front wall has a circular shape with a central axis. The exterior circumferential sidewall is formed around the magnetic body. The exterior circumferential sidewall defines a thickness of the magnetic body. The exterior circumferential sidewall is formed at a first radius from the central axis. The securing assembly is secured to the second end of the catheter body. The securing assembly is actuatable between a locked configuration and an unlocked configuration. The locked configuration is a configuration in which the magnetic implant assembly is secured to the securing assembly. The unlocked configuration is a configuration in which the magnetic implant assembly is not secured to the securing assembly.

In another exemplary embodiment, magnetic implant assembly for an endoscopic anastomosis system is described. The endoscopic anastomosis system includes a main body and one or more protruding portions formed on the main body. The main body includes a first end and a second end. The main body includes a securing assembly secured to the second end of the main body. The securing assembly is actuatable between a locked configuration and an unlocked configuration. The locked configuration is a configuration in which the magnetic implant assembly is secured to the securing assembly. The unlocked configuration is a configuration in which the magnetic assembly is not secured to the securing assembly. The magnetic implant assembly comprises a magnetic body. The magnetic body is formed as a substantially flat body. The magnetic body includes a front wall, rear wall opposite to the front wall, and an exterior circumferential sidewall formed around the magnetic body. The front wall includes a circular shape with a central axis. The exterior circumferential sidewall is formed around the magnetic body. The exterior circumferential sidewall defines a thickness of the magnetic body. The exterior circumferential sidewall is formed at a first radius from the central axis. The one or more protruding portions is formed on the front wall of the magnetic body. The one or more protruding portions includes a first ring shaped protrusion formed on the front wall of the magnetic body. The first ring shaped protrusion is centrally aligned with the central axis. The first ring shaped protrusion includes a first exterior radius from the central axis and a first interior radius from the central axis. The first exterior radius of the first ring shaped protrusion is less than the first radius. Alternatively or in addition, the first exterior radius of the first ring shaped protrusion is equal to the first radius and the magnetic implant assembly further includes an exterior ring shaped body. The exterior ring shaped body is formed around and fixedly secured to the exterior circumferential sidewall of the magnetic body. The exterior ring shaped body includes a front exterior ring shaped portion adjacent to the front wall of the magnetic body and a rear exterior ring shaped portion adjacent to the rear wall of the magnetic body. At least a portion of the front exterior ring shaped body is formed using a material other than a ferromagnetic or magnetic material.

BRIEF DESCRIPTION OF THE DRAWINGS

For a more complete understanding of the present disclosure, example embodiments, and their advantages, reference is now made to the following description taken in conjunction with the accompanying figures, in which like reference numbers indicate like features, and.

5

Figure 5D:
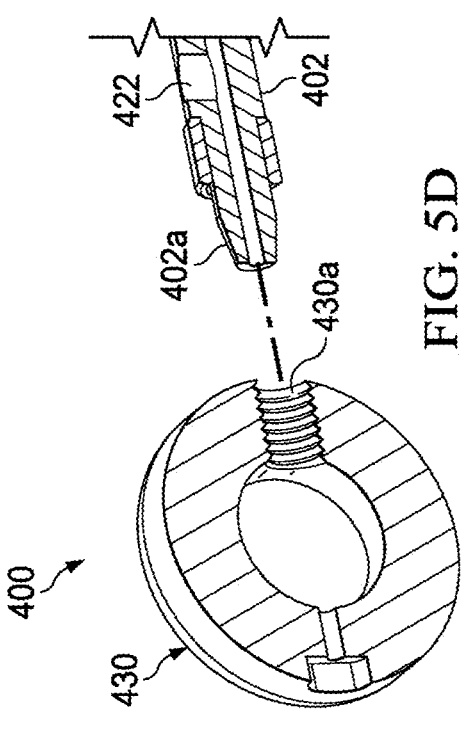
FIG. 5D is a cross-sectional view illustration of another example embodiment of a magnetic implant assembly, a securing assembly, and a second main body assembly.
Figure 5F:
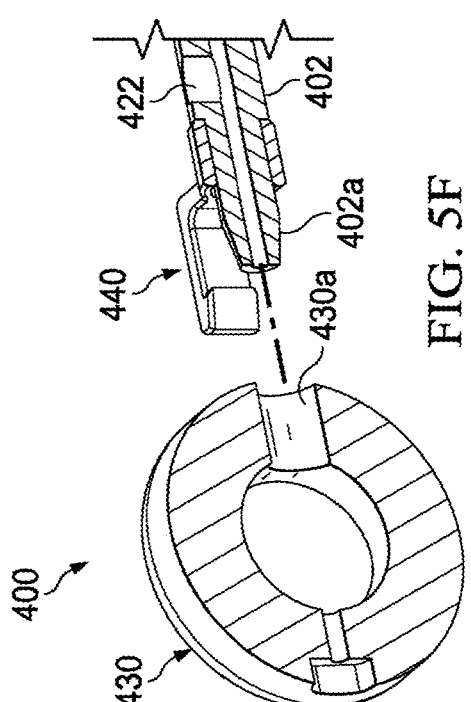
FIG. 5C is a perspective view illustration of another example embodiment of a magnetic implant assembly secured to a second main body assembly via a securing assembly.
FIG. 5E is a perspective view illustration of another example embodiment of a magnetic implant assembly secured to a second main body assembly via a securing assembly.
Figure 5C:
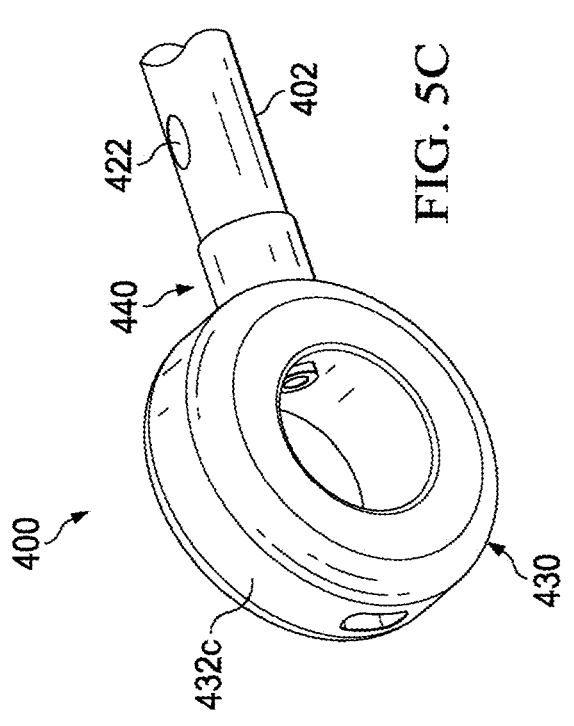
Figure 5E:
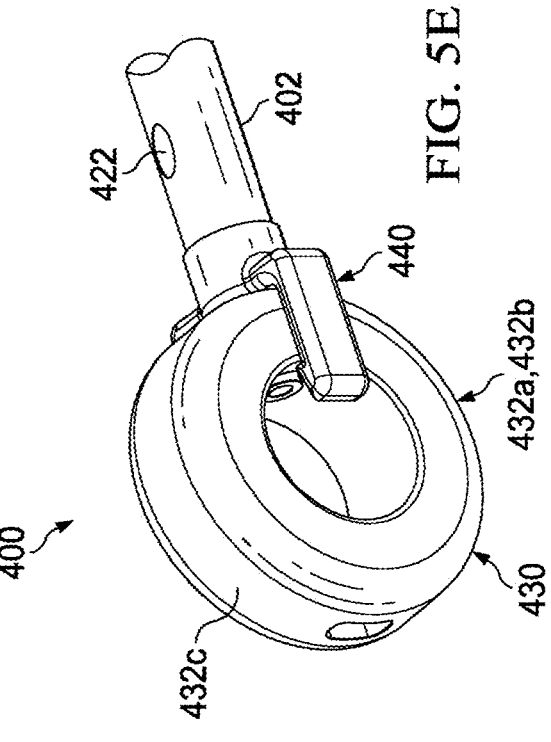
Figure 5G:
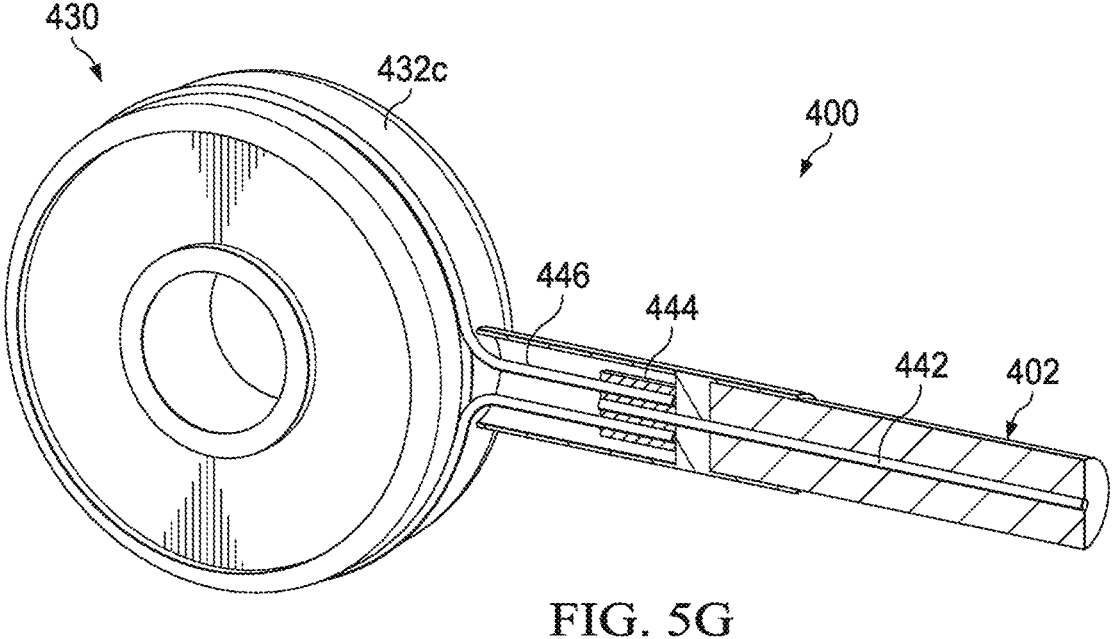
Figure 5H:
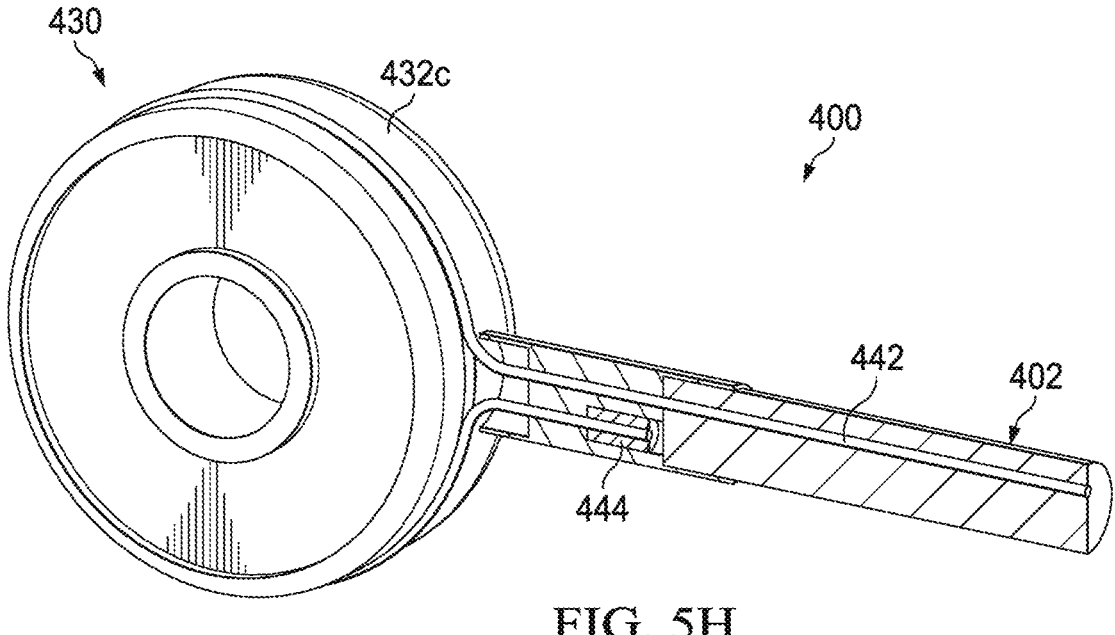
Figures 6A, 6B, 6C, 6D:
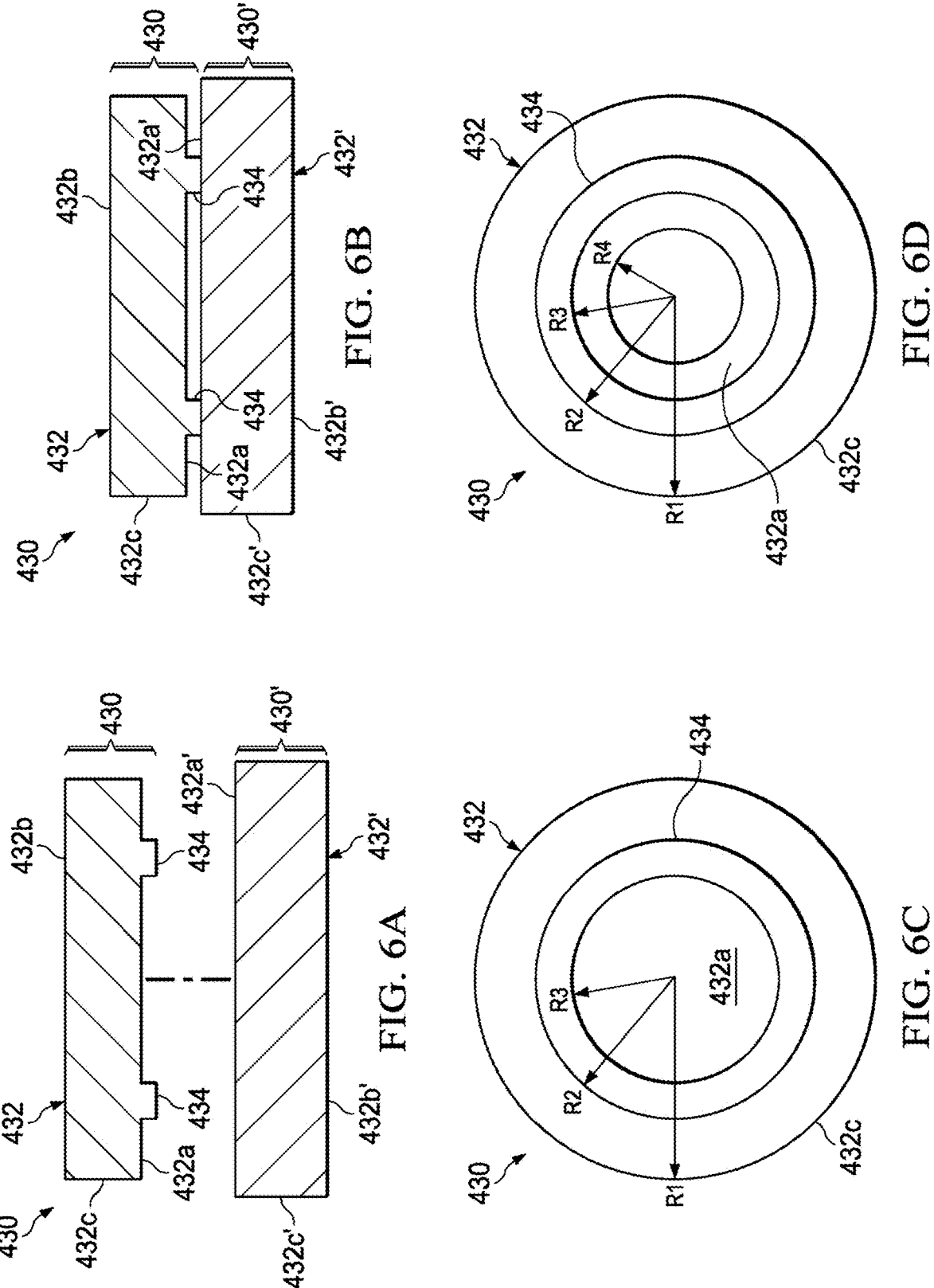
Figures 7A, 7B, 7C, 7D:
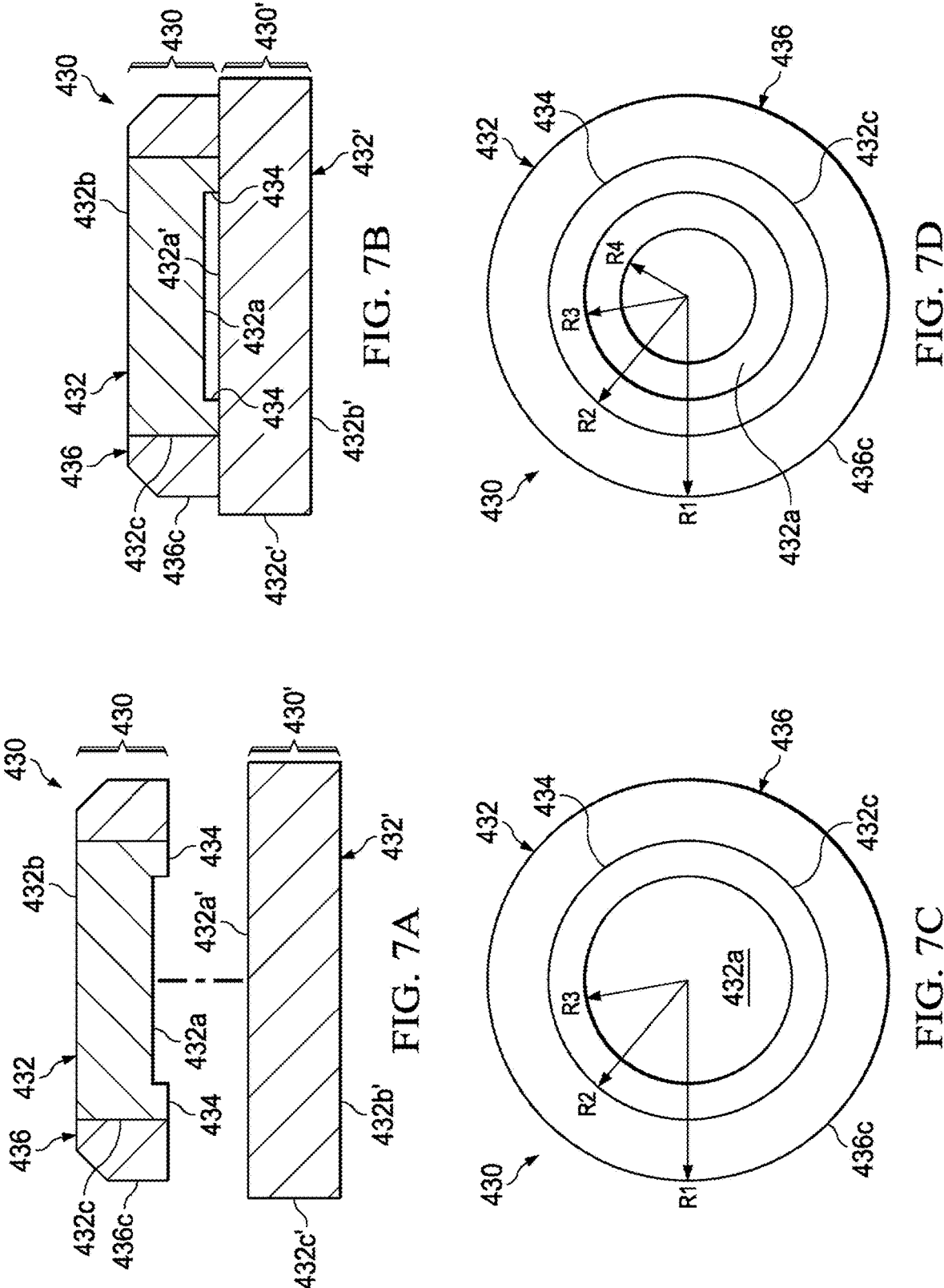
Figures 8A, 8B:
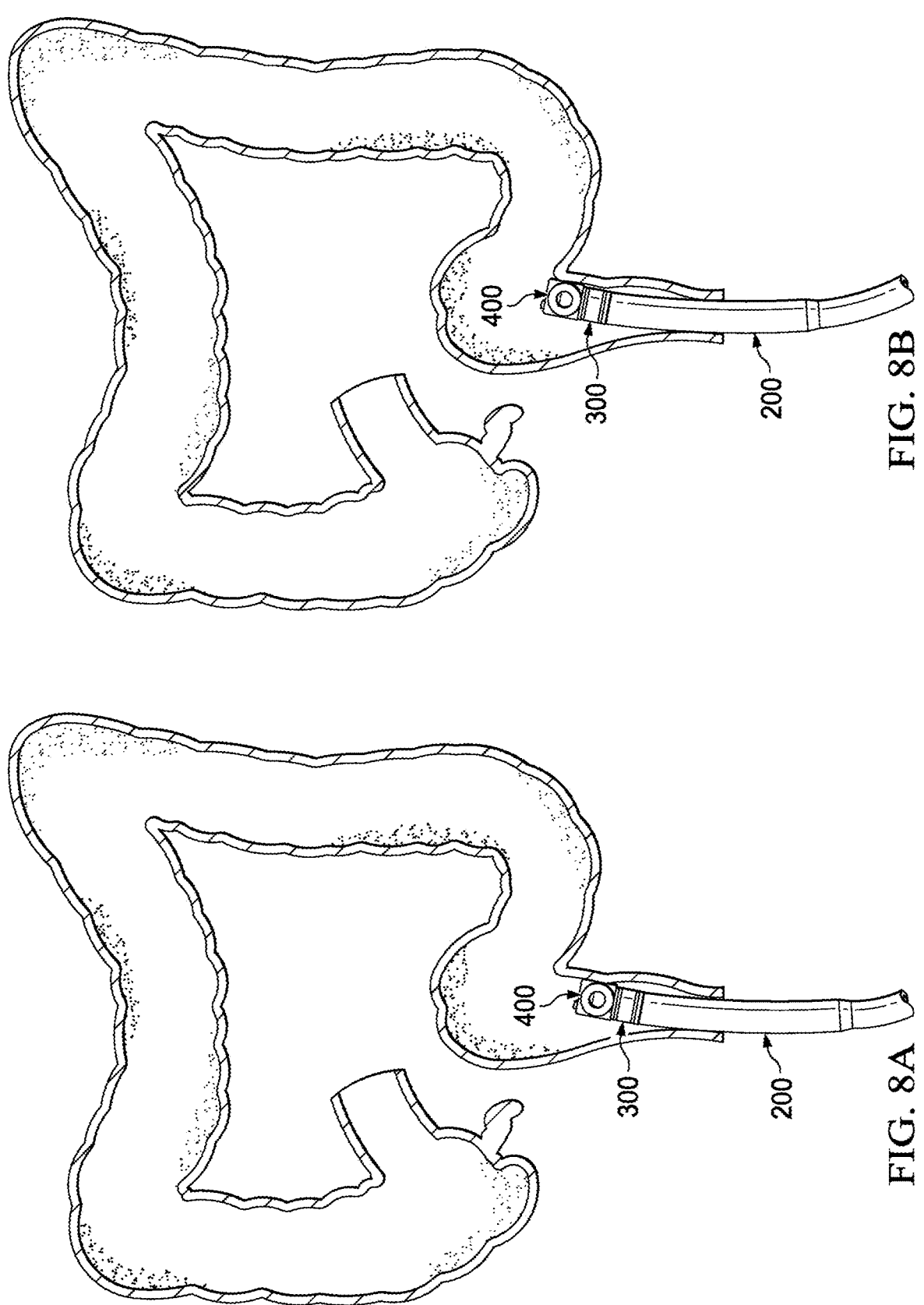
Figure 8C:
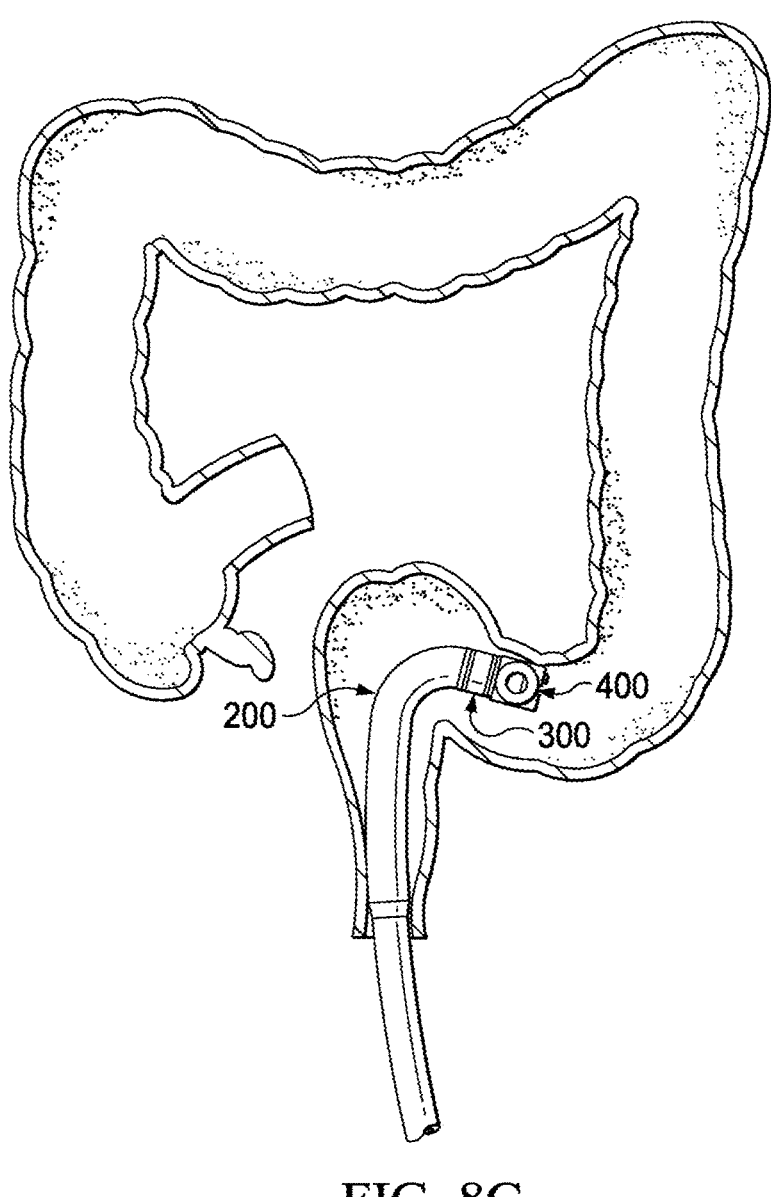
Figures 8D, 8E, 8F:
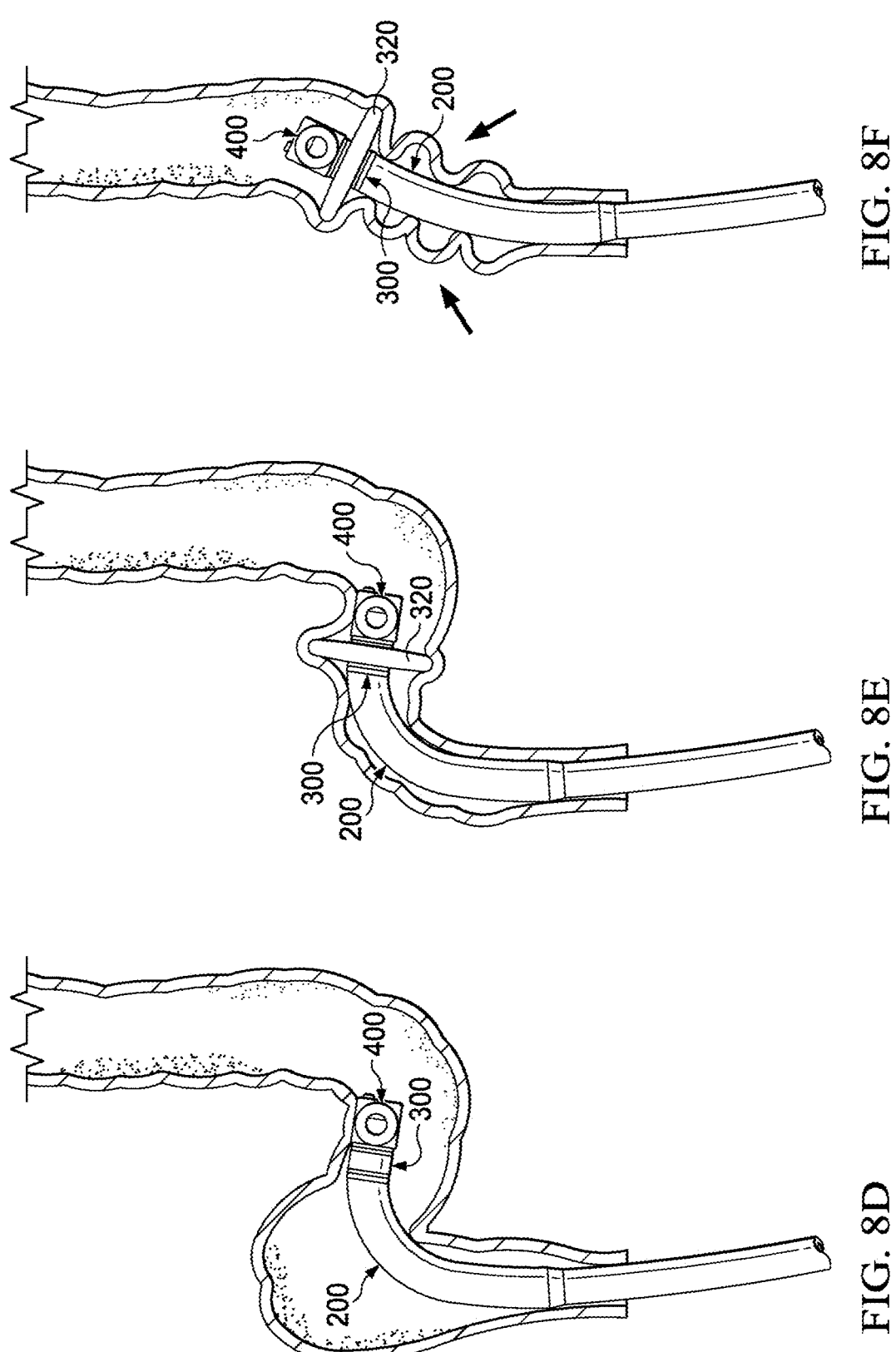
Figures 8G, 8H:
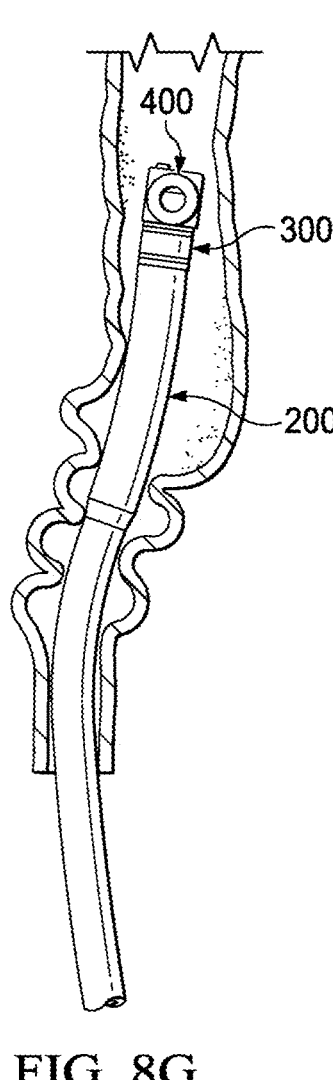
Figures 8I, 8J:
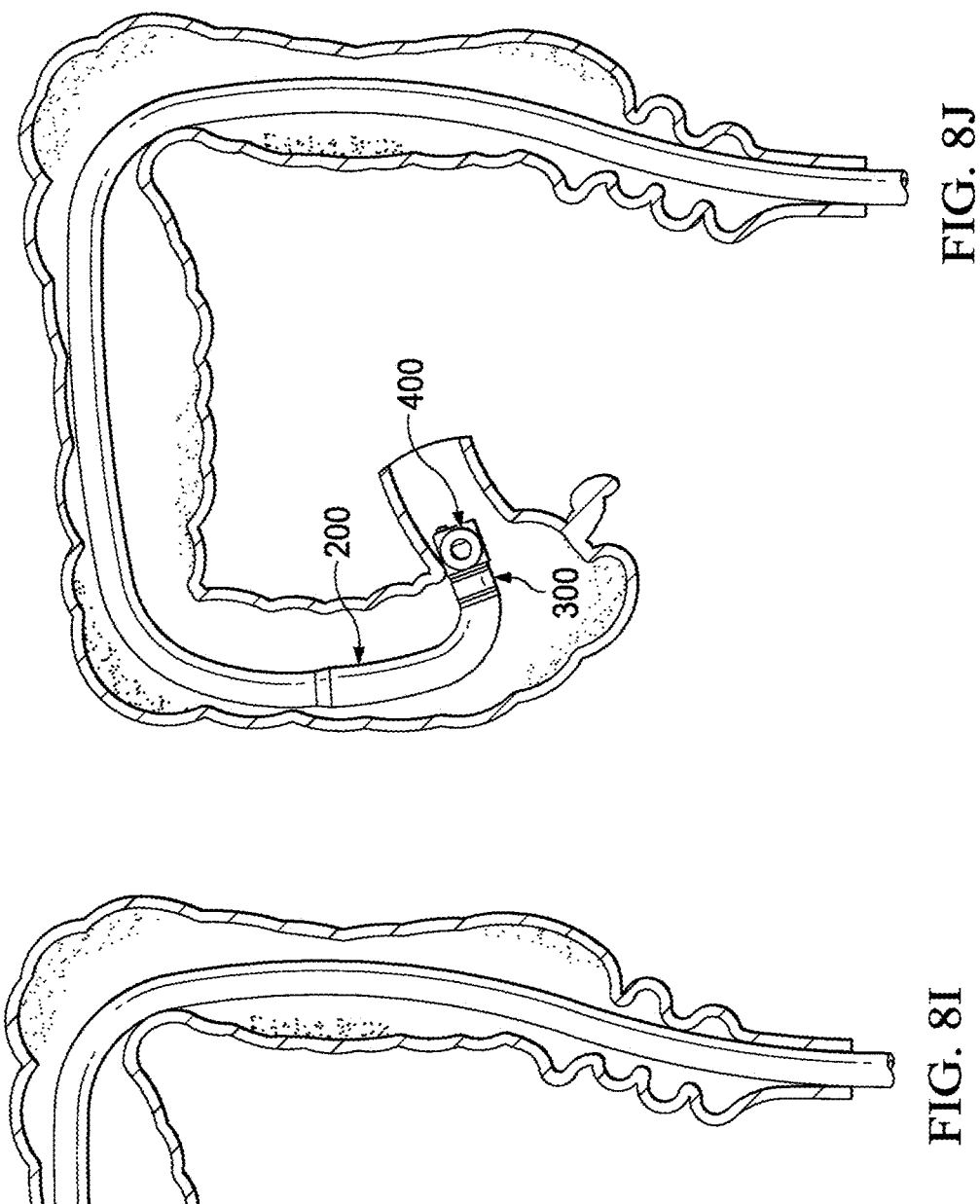
Figures 8K, 8L, 8M:
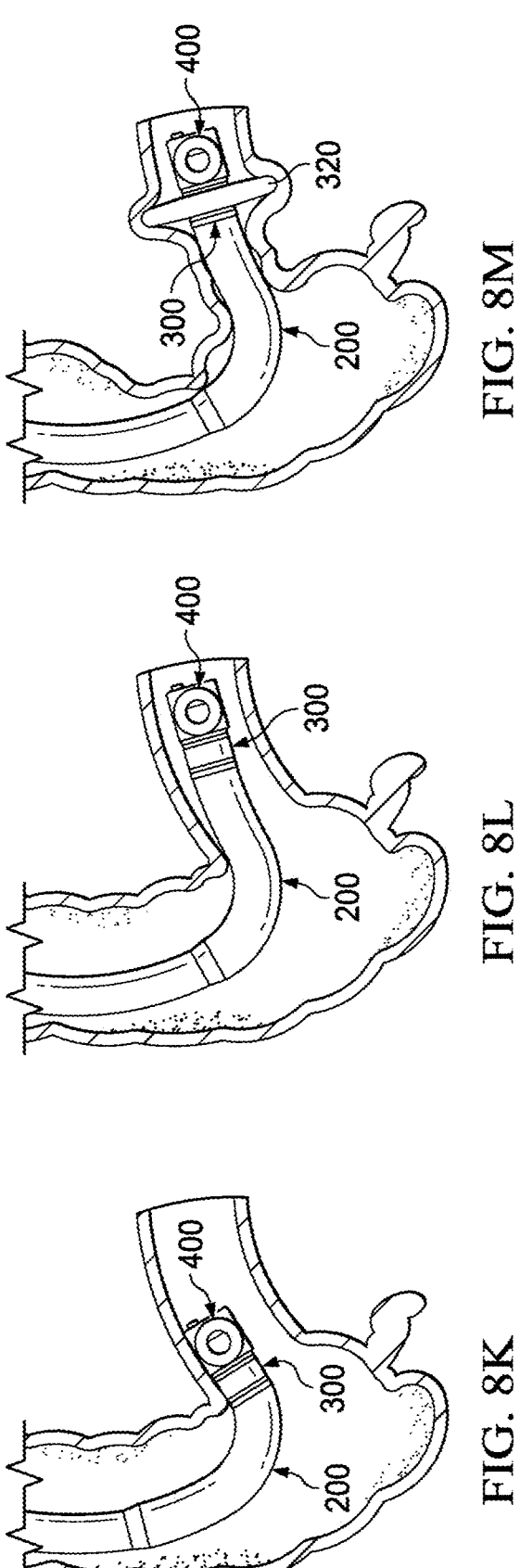
Figure 8N:
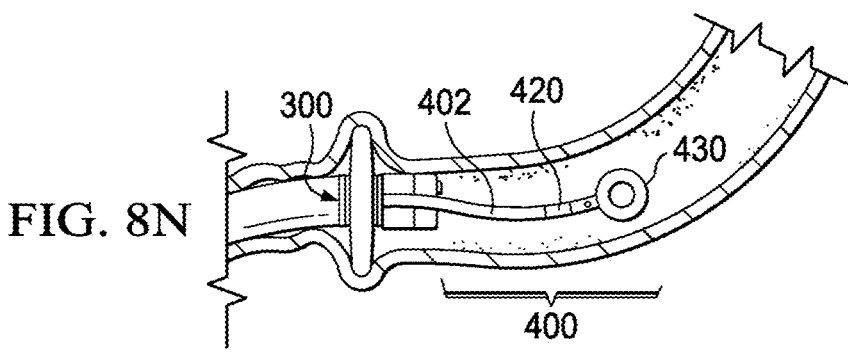
Figure 8O:
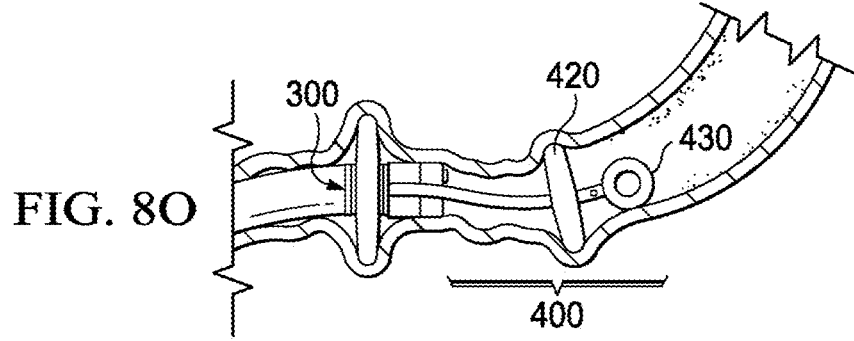
Figure 8P:
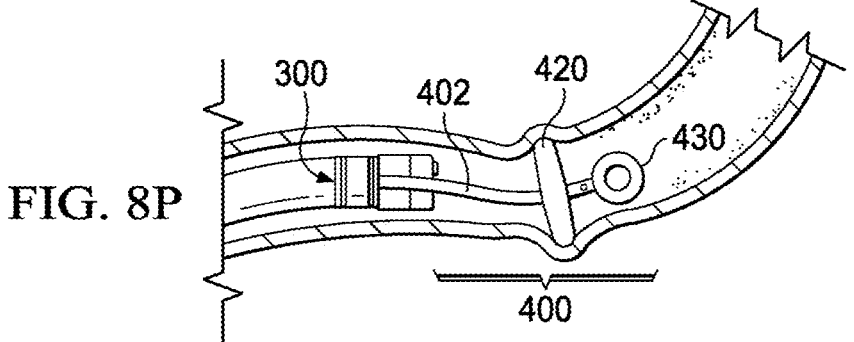
Figures 8Q, 8R, 8S:
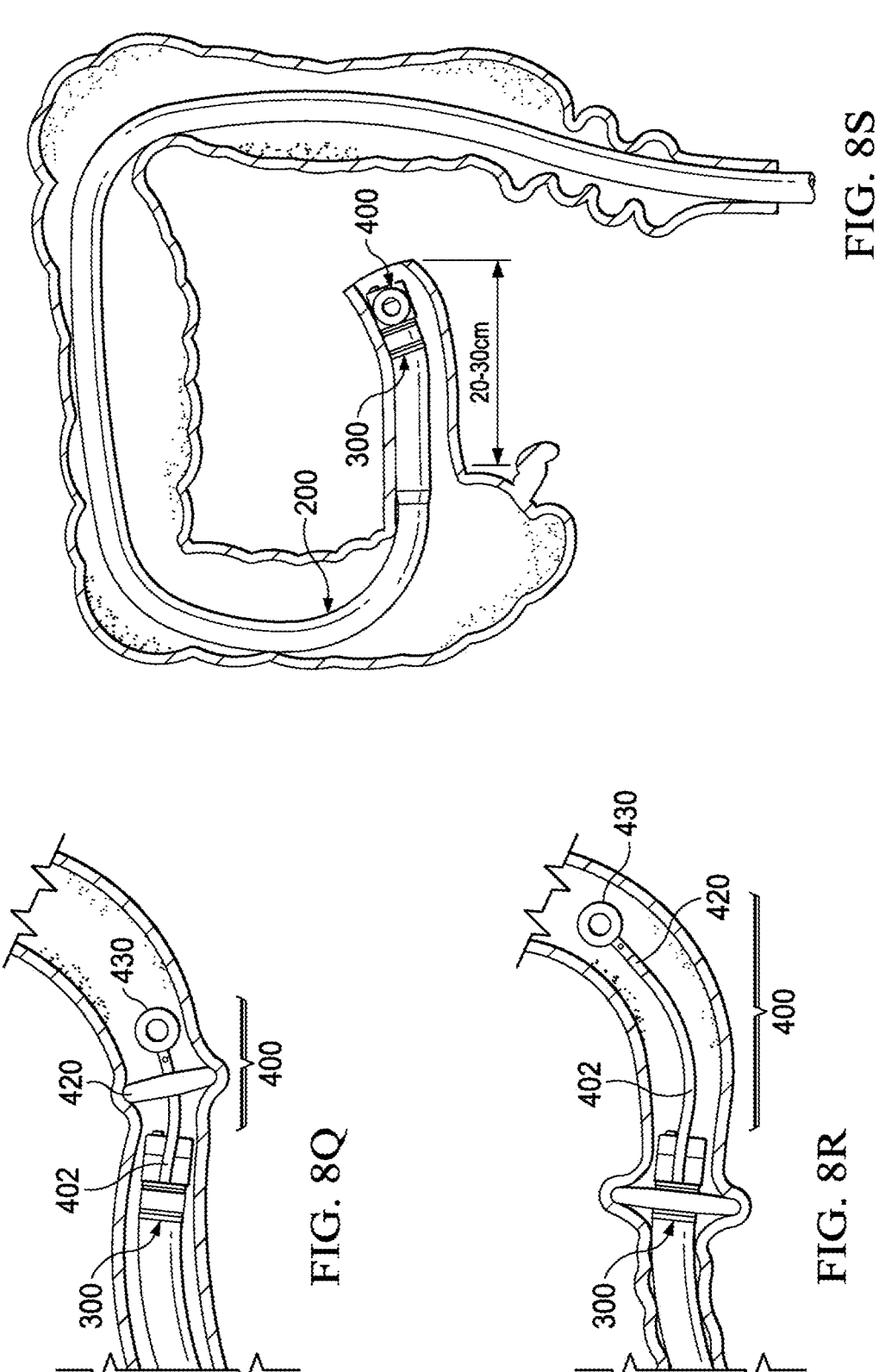

FIG. 5F is a cross-sectional view illustration of another example embodiment of a magnetic implant assembly, a securing assembly, and a second main body assembly;

FIG. 5G is a perspective view illustration of another example embodiment of a magnetic implant assembly secured to a second main body assembly via a securing assembly;

FIG. 5H is a cross-sectional view illustration of another example embodiment of a magnetic implant assembly, a securing assembly, and a second main body assembly;

FIG. 6A is a cross-sectional view illustration of an example embodiment of a magnetic implant assembly and a second magnetic implant assembly;

FIG. 6B is a cross-sectional view illustration of an example embodiment of a magnetic implant assembly magnetically coupled to a second magnetic implant assembly;

FIG. 6C is a top view illustration of an example embodiment of a front wall of a magnetic implant assembly;

FIG. 6D is a top view illustration of another example embodiment of a front wall of a magnetic implant assembly;

FIG. 7A is a cross-sectional view illustration of another example embodiment of a magnetic implant assembly and a second magnetic implant assembly;

FIG. 7B is a cross-sectional view illustration of another example embodiment of a magnetic implant assembly magnetically coupled to a second magnetic implant assembly;

FIG. 7C is a top view illustration of an example embodiment of a front wall of a magnetic implant assembly;

FIG. 7D is a top view illustration of another example embodiment of a front wall of a magnetic implant assembly;

FIGS. 8A-S are illustrations of an example embodiment of a method of delivering a magnetic implant assembly rectally; and FIGS. 9A-I are illustrations of an example embodiment of a method of delivering a magnetic implant assembly orally.

Although similar reference numbers may be used to refer to similar elements in the figures for convenience, it can be appreciated that each of the various example embodiments may be considered to be distinct variations.

Example embodiments will now be described with reference to the accompanying figures, which form a part of the present disclosure and which illustrate example embodiments which may be practiced. As used in the present disclosure and the appended claims, the terms "embodiment," "example embodiment," "exemplary embodiment," and "present embodiment" do not necessarily refer to a single embodiment, although they may, and various example embodiments may be readily combined and/or interchanged without departing from the scope or spirit of example embodiments. Furthermore, the terminology as used in the present disclosure and the appended claims is for the purpose of describing example embodiments only and is not intended to be limitations. In this respect, as used in the present disclosure and the appended claims, the term "in" may include "in" and "on," and the terms "a," "an," and "the" may include singular and plural references. Furthermore, as used in the present disclosure and the appended claims, the term "by" may also mean "from," depending on the context. Furthermore, as used in the present disclosure and the appended claims, the term "if" may also mean "when" or "upon," depending on the context. Furthermore, as used in the present disclosure and appended claims, the words "and/or" may refer to and encompass any or all possible combinations of one or more of the associated listed items.

DETAILED DESCRIPTION

Along with obesity, diabetes is emerging as a primary cause of mortality, morbidity, disability, and discrimination in health care, education and employment. The International Diabetes Federation (IDF) estimates that at present, nearly half a billion people worldwide are living with diabetes, of which low income and middle income countries carry close to 80% of the burden. Moreover, worldwide growth in prevalence is projected to only further worsen over the coming years. It is estimated that by 2045, the global prevalence will increase by 48%, swelling to an estimated 693 million individuals (aged 18-99 years) afflicted. Likewise, there has been a closely paralleled marked increase in obesity. The World Health Organization (WHO) estimates that in 2016, more than 1.9 billion adults, 18 years and older, were overweight. Of these, over 650 million were obese.

The socioeconomic burden associated with these conditions is immense, most of which can be attributed to Diabetes. Hyperglycaemia, a high level of blood glucose, is the hallmark of diabetes. In Type 2 Diabetes (or "T2DM"), hyperglycaemia results from a varying combination of insulin resistance and inadequate insulin production. Chronic hyperglycaemia can cause damage to various organs, leading to the development of disabling and life-threatening complications such as cardiovascular disease, neuropathy, nephropathy, and eye disease leading to retinopathy and blindness. These complications contribute to more frequent hospitalization, increased medical care costs and lower quality of life, and often results in early death. In fact, the IDF estimates that approximately four million people aged between 20 and 79 years died from diabetes in 2017, which equates to about one death every eight seconds. Diabetes accounted for 10.7% of global all-cause mortality among people in this age group, which is higher than the combined number of deaths from infectious diseases (HIV/AIDS, Tuberculosis, and Malaria). Moreover, around 46.1% of deaths due to diabetes in this age bracket were in individuals under the age of 60. In addition to the human burden of diabetes, characterized by premature mortality and low quality of life, there is also a significant economic burden imposed by the disease and its complications. The brunt of this burden is bore upon countries, healthcare systems, and more importantly, directly and direly by inflicted individuals and their families. The global projection for annual healthcare expenditure on diabetes in 2017 was USD 727 billion, corresponding to one for every eight dollars spent on healthcare. These economic costs are ever-increasing, a trend which has been best chronicled and analyzed in the United States (US). The American Diabetes Association has estimated that, after adjusting for inflation, the economic costs of diabetes increased by 26% (from USD 188 billion to USD 237.3 billion) between 2012 to 2017 in the US, which can be attributed to both an increased prevalence of diabetes, as well as an increased cost per person with diabetes. Moreover, after adjusting for both inflation and growth in diabetes prevalence, the excess medical cost per person with diabetes grew by 14% (from USD 8,417 to USD 9,601) in the same 5-year time frame.

Notwithstanding lifestyle and behavioural modification, which have been deemed largely ineffective in the treatment of T2DM, there remains a substantive treatment gap in conventional approaches (surgery and medication) to T2DM treatment that has not been adequately addressed. For surgery, this treatment gap refers to several different cohorts of people, including a large subgroup of individuals that are overweight and diabetic but not considered to be severely obese and therefore do not qualify for traditional surgical procedures. The treatment gap also refers to individuals who do qualify for these procedures but who are unreceptive or unwilling to undergo invasive, anatomy-changing and irreversible operations. Further, the treatment gap also refers to individuals who qualify for surgery, but that are unable to access treatment due to barriers associated with high cost, lack of insurance coverage, and/or available surgical skill. For medication, barriers to access that are commonly cited are high cost, marginal efficacy, and high incidences of side effects. All of these factors put together contribute to the fact that existing surgical procedures, interventions, and medication are used by less than 1% of those eligible worldwide.

Systems, devices, and methods are described herein for use in delivering and magnetically coupling magnetic implant assemblies so as to create an anastomosis in adjacent points of the digestive tract (between the duodenum and ileum, or the jejunum and the ileum). It is recognized in the present disclosure that such resulting alternate "pathway" or "short-cut" (i.e., the anastomosis) may provide an alternate pathway for nutrient-rich chyme to enter the ileum more quickly and distally, which may result in avoiding absorption in the foregut, triggering early satiety, and/or improving glucose metabolism (e.g., by mediating a supposed "incretin effect", which is characterized by an increased secretion of Glucagon-like peptide (GLP-1), a gut hormone that stimulates insulin secretion, gene expression, and β-cell growth). In this regard, diabetes control may result from such expedited delivery of nutrient-rich chyme to the distal intestines, and may result in the emanation of a physiological signal leading to improved glucose metabolism. It is to be understood that the principles described in the present disclosure may be applied outside of the context of endoscopic anastomosis procedures, such as performing diagnostic procedures, surgical or therapeutic procedures, scientific experiments, and/or other procedures in the same and/or other environments, cavities, and/or organs not described in the present disclosure without departing from the teachings of the present disclosure.

Example embodiments will now be described below with reference to the accompanying figures, which form a part of the present disclosure.

Example Embodiments of the Endoscopic Anastomosis System (e.g., Endoscopic Anastomosis System 100)

Figure 1A:
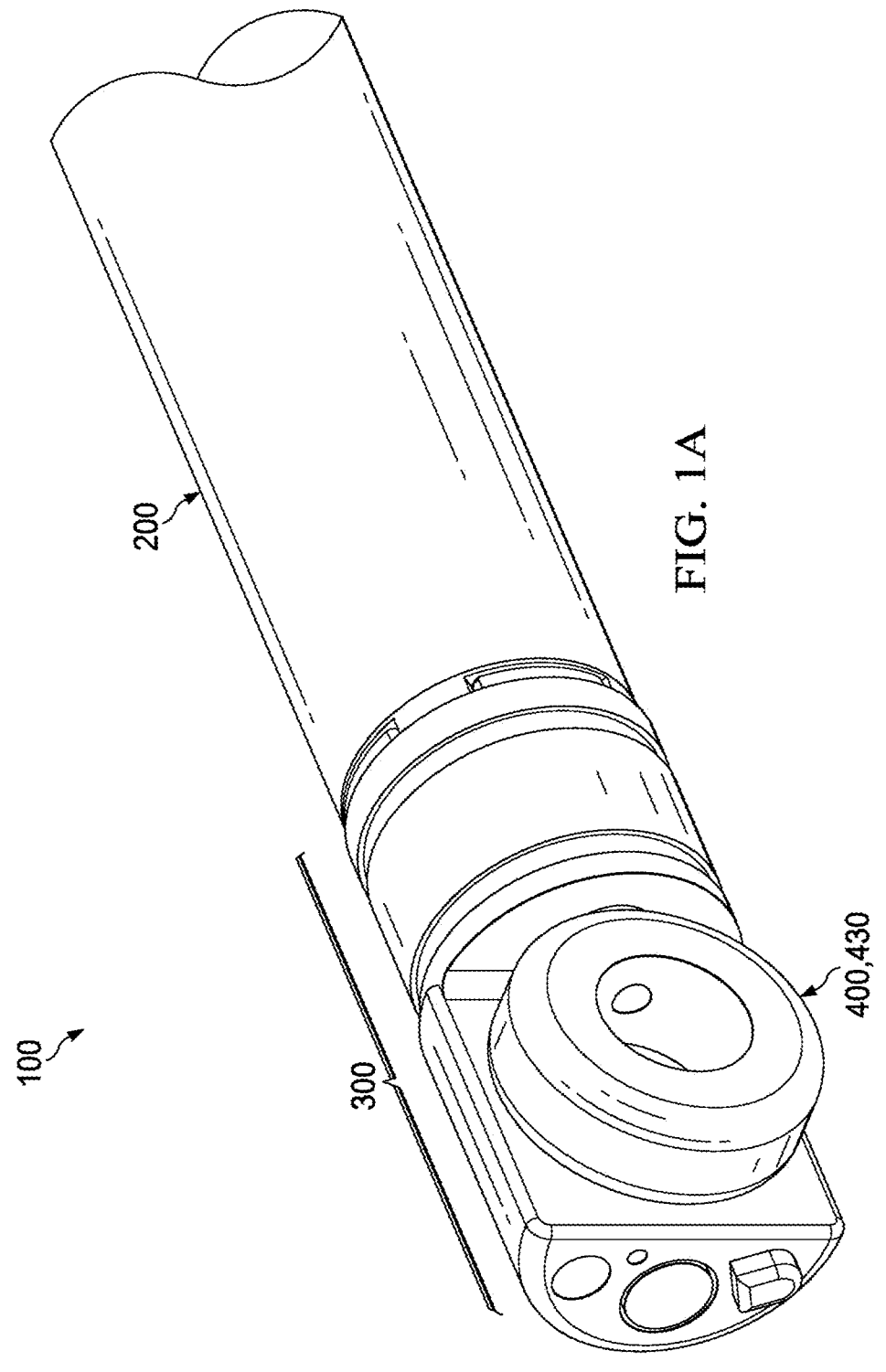
FIG. 1A is a perspective view illustration of an example embodiment of an endoscopic anastomosis system.
Figures 1B, 1C:
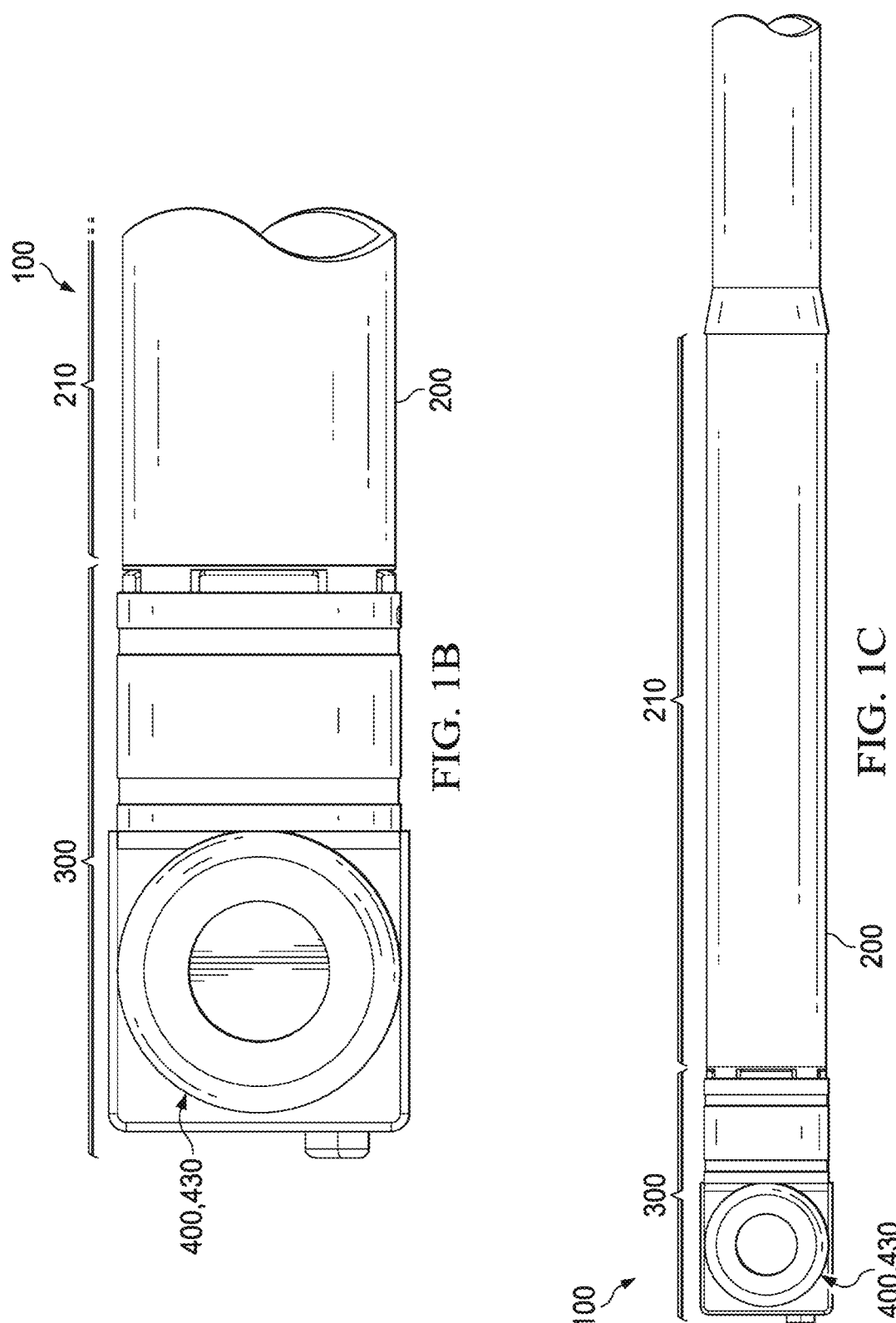
FIG. 1B is a side view illustration of an example embodiment of an endoscopic anastomosis system.
FIG. 1C is another side view illustration of an example embodiment of an endoscopic anastomosis system.

FIG. 1A, FIG. 1B, and FIG. 1C illustrate different views of an example embodiment of an endoscopic anastomosis system (e.g., system 100). The system 100 may be configurable or configured to be inserted through a natural orifice (e.g., rectum) of a patient to deliver a first magnetic implant body (or magnetic body) 430 into a cavity (e.g., colon or ileocecal valve) of the patient. A complimentary, corresponding, or associated second system 100 adapted to be inserted through another natural orifice (e.g., mouth) of the patient delivers a second magnetic implant body 430 into an adjacent cavity (e.g., duodenum or jejunum) of the patient, which is then magnetically coupled through one or more cavity walls to the first magnetic implant body 430. Together, the first and second magnetic implant bodies 430 are configured to form an anastomosis through the one or more cavity walls.

Figure 2:
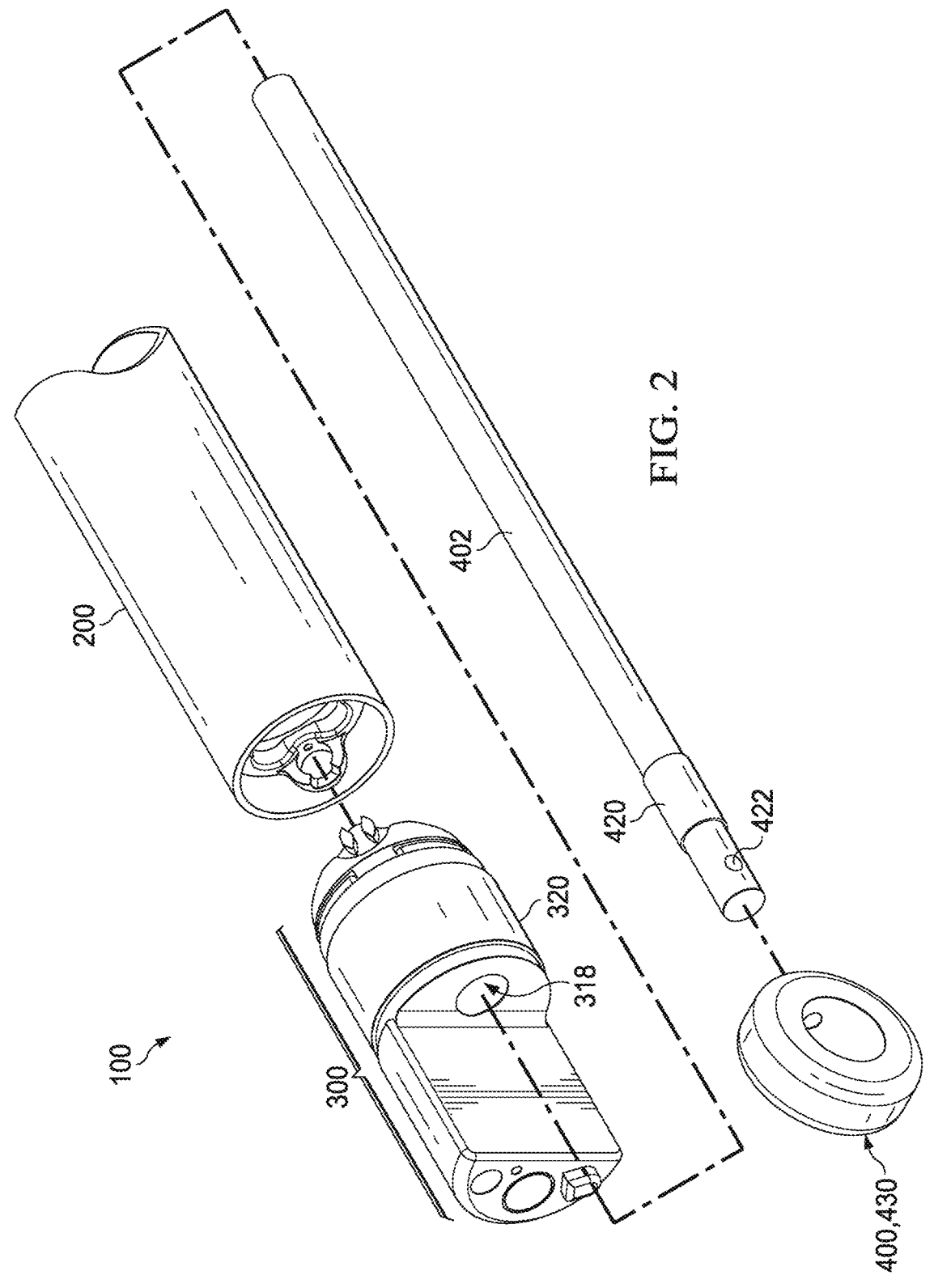
FIG. 2 is a perspective view illustration of an example embodiment of some of the elements of an endoscopic anastomosis system separated from one another.

Each system 100 includes one or more elements. For example, as will be further described in the present disclosure, each system 100 includes a first main body assembly 200 (or first main body 200). Each system 100 also includes a head assembly 300. The head assembly 300 is secured to an end of the first main body assembly 200 (e.g., referred to herein as the second end 203 of the first main body assembly 200, distal end of the first main body assembly 200, or end that is inserted into a cavity of a patient). Although the head assembly 300 may be referred to in the present disclosure as being a separate element from (and secured to) the first main body assembly 200, it is to be understood that the head assembly 300 may also be considered as an element or part of the first main body assembly 200 without departing from the teachings of the present disclosure. Each system 100 also includes a second main body assembly 400. At least a portion of the second main body assembly 400 is housed in an interior of the head assembly 300, and at least a portion of the second main body assembly 400 is provided/inserted through an opening 318 (referred to herein as a "second main body assembly opening" 318, "catheter body opening" 318, or the like) of the head assembly 300. Furthermore, at least a portion of the second main body assembly 400 is housed in the first main body assembly 200. In example embodiments, the first and second main bodies 200, 400 are slidable relative to one another. Each system 100 also includes a magnetic implant assembly 430. Each system 100 also includes a securing assembly 440. Although the magnetic implant assembly 430 and/or the securing assembly 440 may be referred to in the present disclosure as being separate element(s) from (and secured to) the second main body assembly 400, it is to be understood that the magnetic implant assembly 430 and/or the securing assembly 440 may also be considered as an element or part of the second main body assembly 400 without departing from the teachings of the present disclosure. For ease of reference, FIG. 2 illustrates a view of these elements separated from one another.

As used in the present disclosure, when applicable, one or more elements of each system 100 may be controlled, in part or in whole, directly or indirectly, by or in cooperation with one or more processors, controllers, computing devices, processors, servers, systems, cloud-based computing, artificial intelligence (AI), or the like (referred to herein as a "controller", "processor", or the like) (not shown) and/or one or more surgeon consoles (not shown, which may be any console, or the like, for one or more surgeons to perform one or more actions described in the present disclosure). Such controller and/or surgeon console may be in communication with and/or control one or more external systems/devices (e.g., external pressure source for providing negative and/or positive pressure, etc.) (not shown). Such controller may be any processor, server, system, device, computing device, controller, microprocessor, microcontroller, microchip, semiconductor device, or the like, configurable or configured to perform, among other things, a processing and/or managing of information, searching for information, identifying of information, data communications, processing information and/or making one or more decisions via artificial intelligence, machine learning, deep learning, or the like, and/or any one or more other actions described in the present disclosure. Alternatively or in addition, such controller (and/or its elements) may include and/or be a part of a virtual machine, processor, computer, node, instance, host, or machine, including those in a networked computing environment. As used in the present disclosure, a communication channel, or the like, may be or include a collection of devices and/or virtual machines connected by communication channels that facilitate communications between devices and allow for devices to share resources. Such resources may encompass any types of resources for running instances including hardware (such as servers, clients, mainframe computers, networks, network storage, data sources, memory, central processing unit time, scientific instruments, and other computing devices), as well as software, software licenses, available network services, and other non-hardware resources, or a combination thereof. A communication channel may include, but is not limited to, the internet, intranets, WiFi systems, GPS systems, location systems, location-based service systems, computing grid systems, peer to peer systems, mesh-type systems, distributed computing environments, cloud computing environment, telephony systems, voice over IP (VoIP) systems, etc. Such communication channels may include hardware and software infrastructures configured to form a virtual organization comprised of multiple resources which may be in geographically disperse locations. Communication channel may also refer to a communication medium between processes on the same device or system.

These and other elements of the system 100 will now be described with reference to the accompanying figures.
The First Main Body Assembly (e.g., First Main Body Assembly 200).

Figures 3A, 3B:
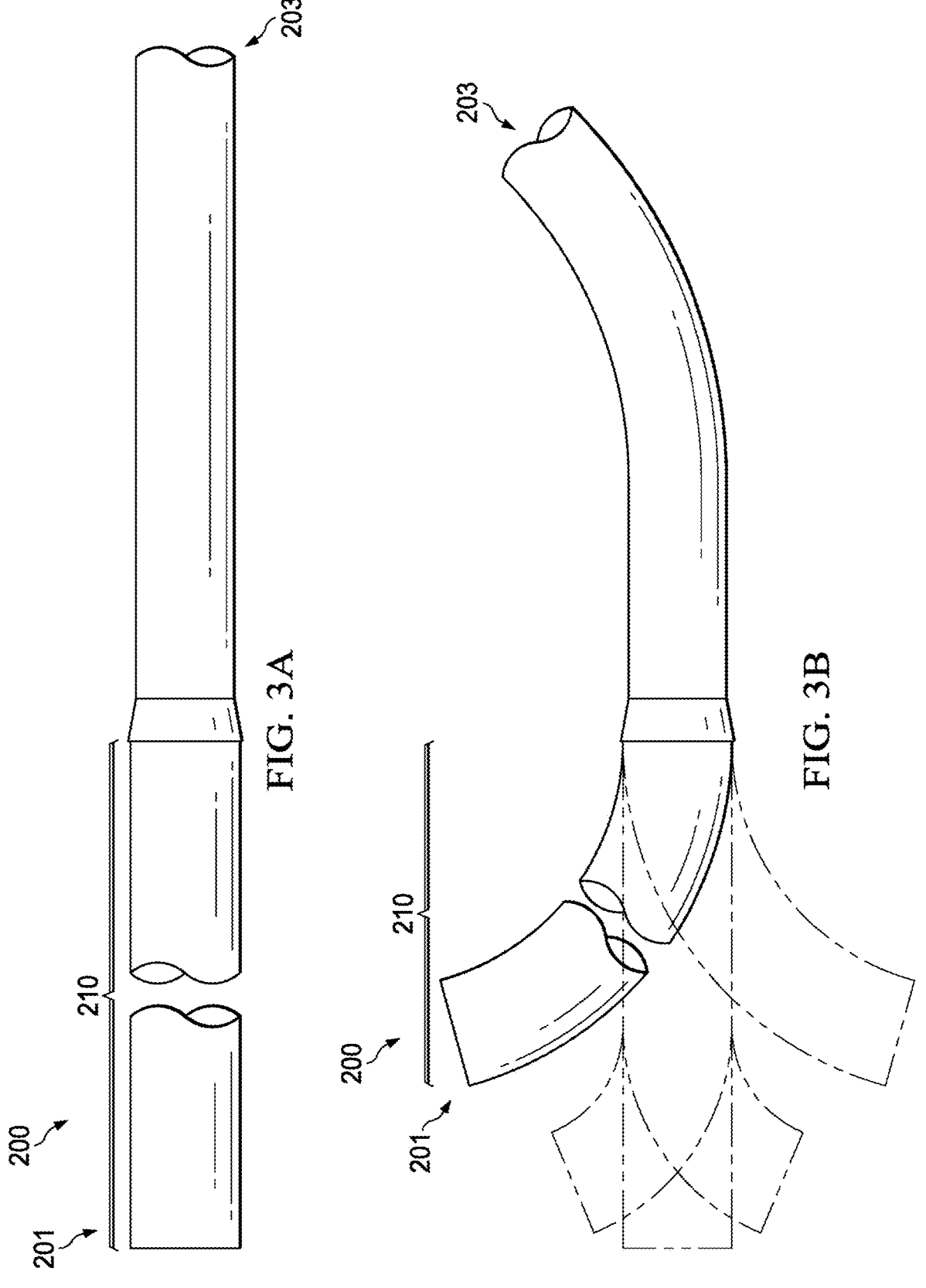
FIG. 3A is a side view illustration of an example embodiment of a first main body assembly.
FIGS. 3B and 3C are side view illustrations of an example embodiment of a first main body assembly and the first bendable section configured to bend.
Figure 3C:
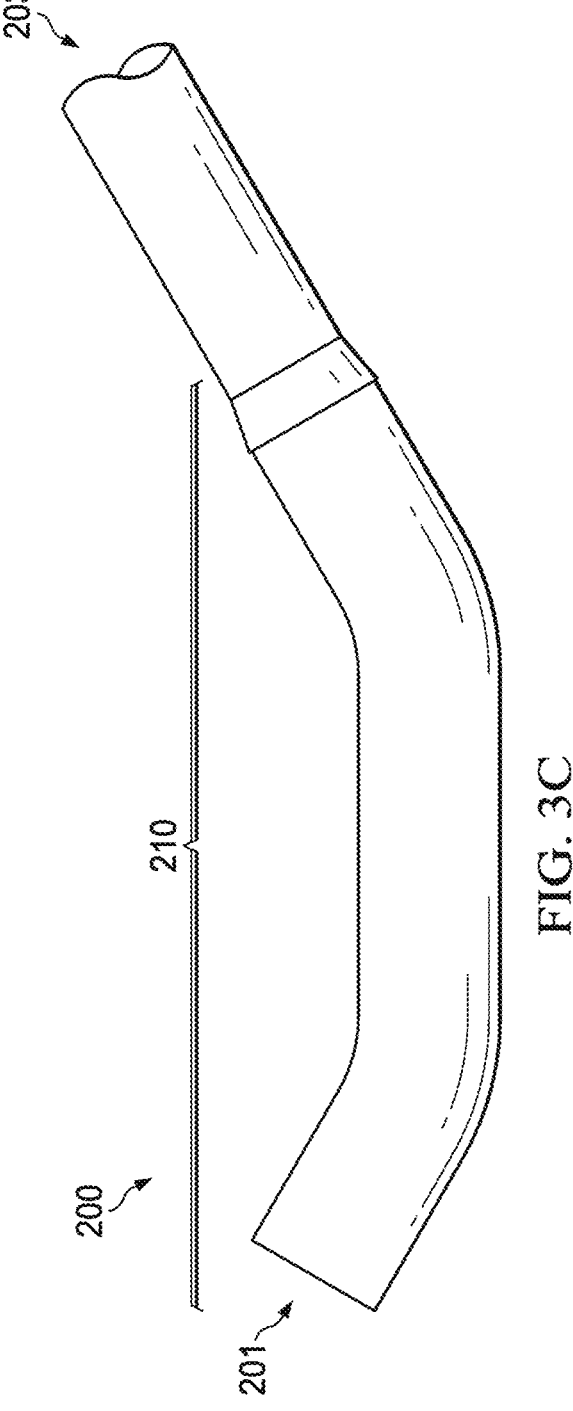

As illustrated in at least FIG. 3A, FIG. 3B and FIG. 3C, each system 200 includes a first main body assembly 200. The first main body assembly 200 may include an elongated tubular structure having a first end 201 (or "proximal end" 201) and a second end 203 (or "distal end" 203). The first main body assembly 200 may include a flexible body or tube having one or more internal channels (not shown). For example, the one or more internal channels may be provided for a plurality of actuation control members (e.g., cables, wires, tendons, or the like) to extend from the controller and/or surgeon console (at or near the first end 201) to a portion of the second end 203 (e.g., to the first bendable section 210). As another example, the one or more internal channels may be provided to house the second main body assembly 400 (which may extend from the controller and/or surgeon console (at or near the first end 201) and through the second main body assembly opening 318 of the head assembly 300. In this regard, the second main body assembly 400 and the first main body assembly 200 may be configured to slide relative to one another. As another example, the one or more internal channels may be provided to enable negative pressure and/or positive pressure to be supplied from one or more external pressure sources (not shown) to the one or more pressure openings 332, 334, 422. As another example, the one or more internal channels may be provided for positive pressure and/or negative pressure to be supplied from one or more external pressure sources (not shown) to the first and second expandable members 320, 420. As another example, the one or more internal channels may be provided for washing fluid, positive pressure, and/or negative pressure to be supplied from one or more external pressure sources (not shown) to the first cleansing assembly 338. As another example, the one or more internal channels may be provided for electrical and/or data cables to extend to the first image capturing assembly 336. As another example, the one or more internal channels may be provided for cables to extend to one or more sensors (e.g., for haptic feedback, temperature sensor, pressure sensor, etc., not shown), etc. Other internal channels for other purposes are also contemplated in the present disclosure. It is to be understood that an internal channel of the first main body assembly 200 may be any channel (including those that are wholly or partially within the first main body assembly), and may include a smaller tube, or the like, provided in a larger channel or tube. It is also to be understood that an internal channel of the first main body assembly 200 may extend beyond the first end 201 and/or second end 203 of the first main body assembly 200.

As illustrated in at least FIGS. 1A and 1B, the second end 203 of the first main body assembly 200 may be securable or secured to (and in example embodiments, detachable from) a connector portion 302 of the head assembly 300.

The first main body assembly 200 includes a first bendable section (e.g., first bendable section 210) at the second end 203 of the first main body assembly 200. Although not illustrated in the Figures, the second end 203 of the first main body assembly 200 may also include one or more expandable members (e.g., similar to the first expandable member 320 and/or second expandable member 420) and/or one or more pressure openings (e.g., similar to the first pressure opening 332 and/or second pressure opening 422). Such one or more pressure openings may be provided before and/or after such one or more expandable members, and such one or more pressure openings and/or one or more expandable members may be provided before and/or after the first bendable section 210. In some example embodiments, such expandable member(s) and/or pressure opening(s) of the first main body assembly 200 may be in addition to or replace the first expandable member 320 and/or the first pressure opening 332 of the head assembly 300.

In an example embodiment, the first bendable section 210 is configurable or configured to guide, turn, bend, and/or steer (referred to herein as "bend", "bending", or the like) the system 100 in any one or more of a plurality of available directions and/or one or more of a plurality of locations along the first bendable section 210. This may be desirable when the system 100 is being advanced forward into a body cavity, such as a colon or small bowel, and the system 100 reaches a bend, turn, or the like in the body cavity. Alternatively or in addition, such bending may be desirable when a particular area of the interior wall of the body cavity needs to be viewed and/or actioned (e.g., delivering of the magnetic implant body 430). Such bending of the first bendable section 210 may be achievable or achieved by selectively configuring one or more locations along the first bendable section 210 to bend (e.g., away from a center axis formed by the first bendable section 210). Such selective configuring may include selecting one or more locations along the first bendable section 210 to bend from among a plurality of bendable location(s) along the first bendable section 210. FIG. 3B illustrates an example of bending of the first bendable section 210. Selective configuring may also include selecting, for each location along the first bendable section 210, a degree of curvature for the bending from among a plurality of available degrees of curvature. Selective configuring may also include selecting, for each location along the first bendable section 210, one or more directions for the bending from among a plurality of available directions, etc.

The bending of the first bendable section 210 may be selectively controllable by controlling an amount of force (e.g., tension via pulling or pushing) applied (increased, decreased, maintained, or not applied) to one or more actuation control members (not shown) and/or selecting one or more of the actuation control members to selectively control (i.e., which actuation control member will receive an increase in applied force, decrease in applied force, no change in applied force, and/or no applied force). In an example embodiment, the first bendable section 210 may include a serially (or linearly) connected arrangement of a plurality of bendable subsections (not shown). Each bendable subsection may include one or more distal termination points for receiving, securing, terminating, and/or connecting one or more actuation control members.

Each of the bendable subsections may include one or more internal cavities or channels for, among other things, enabling one or more actuation control members to extend through, enabling negative pressure and/or positive pressure to be provided to the one or more pressure openings 332, 422, enabling positive pressure and/or negative pressure to be provided to the first expandable member 320, enabling positive pressure and/or negative pressure to be provided to the second expandable member 420, enabling fluid and/or positive pressure (and/or negative pressure) to be provided to the first cleansing assembly 338, enabling electrical and/or data cables to extend to the first image capturing assembly 336, etc.

The distal termination points may be provided in any shape or form so long as it enables the receiving, connecting, terminating, and/or securing of the distal end of one or more actuation control members. For example, the distal termination point may be an opening, connector, termination, hook, etc. A degree of bending of one or more of the bendable locations of the first bendable section 210 may be between about 0 to 210 degrees from a center axis in example embodiments.

In an example embodiment, the first main body assembly 200 may have a length between about 1600 mm to about 2200 mm, and a diameter between about 12 mm to about 18 mm. The first main body assembly 200 may be formed having one or more of a plurality of cross-sectional shapes, including a circular cross-section, elliptical cross-section, etc. Other dimensions and shapes are also contemplated without departing from the teachings of the present disclosure. A length of the first bendable section 210 may be between about 70 mm to about 130 mm, and a diameter of the first bendable section 210 may be between about 12 mm to about 18 mm in example embodiments. Other dimensions are also contemplated without departing from the teachings of the present disclosure.

The Head Assembly (e.g., Head Assembly 300).

Figure 4A:
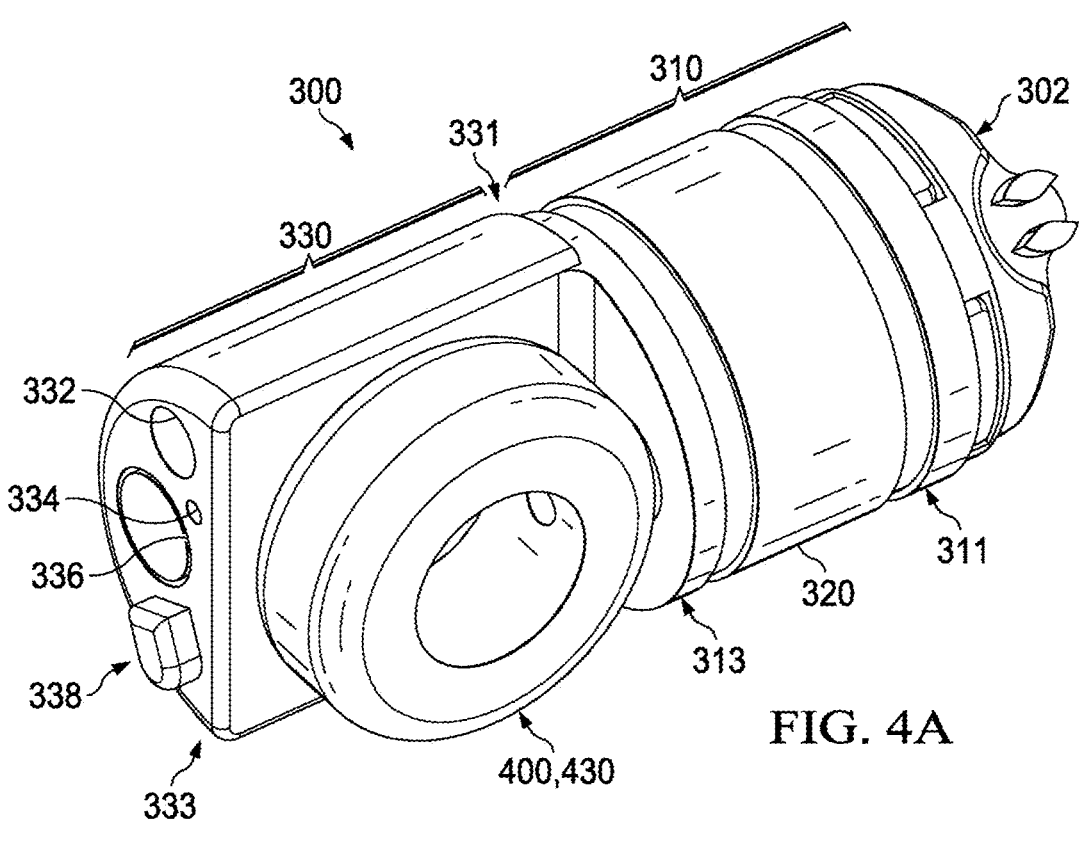
FIG. 4A is a perspective view illustration of an example embodiment of a head assembly with a magnetic implant assembly.
Figure 4B:
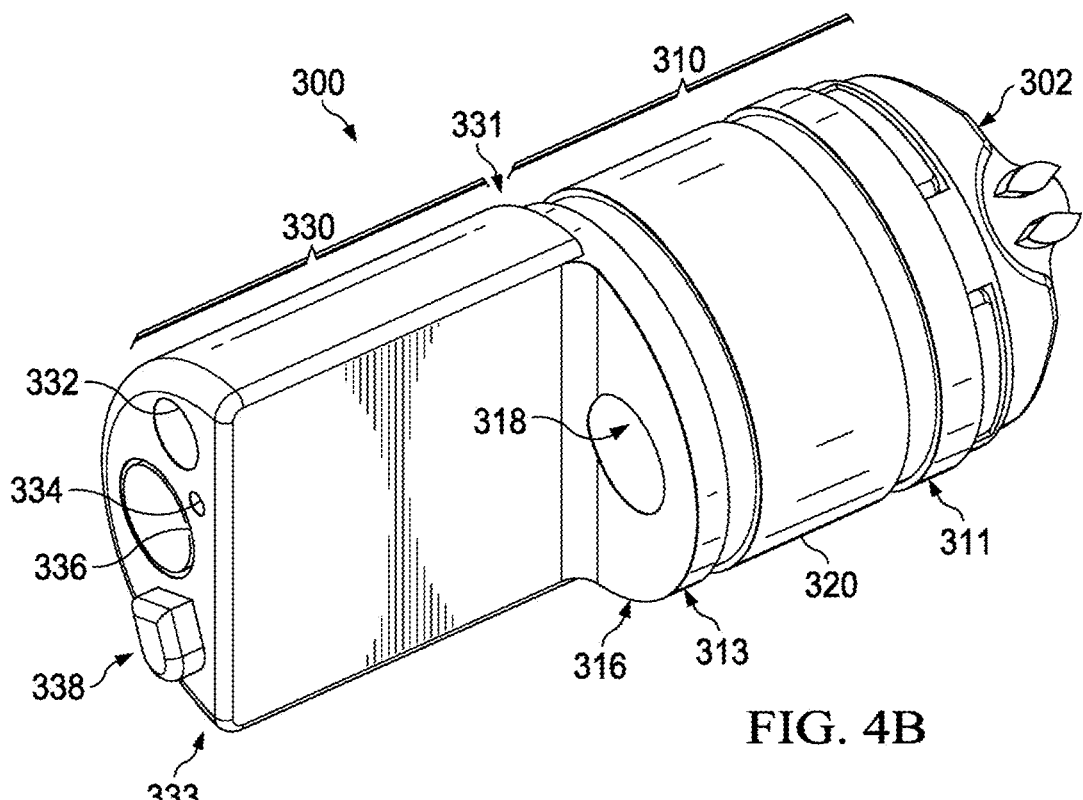
FIG. 4B is a perspective view illustration of an example embodiment of a head assembly without a magnetic implant assembly.

As illustrated in at least FIG. 2, FIG. 4A, and FIG. 4B, each system 200 includes a head assembly 300. The head assembly 300 includes a head assembly body 300. The head assembly 300 also includes one or more first expandable members 320. The head assembly 300 also includes one or more first pressure ports 332. The head assembly 300 also includes a second main body opening 318. The head assembly 300 also includes one or more insufflation ports 334. The head assembly 300 also includes one or more first image capturing assemblies 336. The head assembly 300 also includes one or more first cleansing assemblies 338.

These and other elements of the head assembly 300 will now be described with reference to the accompanying figures.

The Head Assembly Body (e.g., Head Assembly Body 300).

As illustrated in at least FIGS. 2 and 4A-B, the head assembly 300 includes a head assembly body 300. The head assembly body 300 includes a connector portion 302 at a first end of the head assembly body 300 for securing to the second end 203 of the second main body assembly 200. The head assembly body 300 also includes a first region, portion, or the like (referred to herein as the "first region" 310) and a second region, portion, or the like (referred to herein as the "second region" 330). A first end 311 of the first region 310 is secured to the second end 203 of the second main body assembly 200 via the connector portion 302, and at least a portion of a second end 313 of the first region 310 is secured to the first end 331 of the second region 330.

In example embodiments, the second end 313 of the first region 310 of the head assembly body 300 includes a first section 316 (as illustrated in at least FIG. 4B) and a second section (not shown) adjacent to the first section 316. The second section of the first region 310 is secured to the first end 331 of the second region 330 of the head assembly body 300. The first section 316 of the first region 310 includes a second main body assembly opening 318 (or second main body opening 318 or catheter body opening 318 or catheter opening 318). The second main body assembly opening 318 is configured to house at least a portion of the second main body assembly 400. That is, at least a portion of the second main body assembly 400 is provided/inserted through the second main body assembly opening 318. In this regard, the second main body 402 is moveable/slidable relative to the head assembly body 300. The first region 310 also includes one or more other pressure openings (not shown) for providing positive and/or negative pressure to an interior portion of the first expandable member 320 (e.g., to expand, maintain, or contract a volume of the first expandable member 320). The first region 310 also includes one or more internal cavities or channels. For example, the one or more internal cavities or channels may house at least a portion of a second end of the second main body 402 of the second main body assembly 400. The one or more internal cavities or channels may also house the plurality of actuation control members (e.g., cables, wires, tendons, or the like, as described in the present disclosure) that control the second bendable section 410 of the second main body assembly 400. As another example, the one or more internal cavities or channels may be provided to enable negative pressure and/or positive pressure to be supplied from one or more external pressure sources (not shown) to one or more pressure openings 332, 334, 422. As another example, the one or more internal cavities or channels may be provided for positive pressure and/or negative pressure to be supplied from one or more external pressure sources (not shown) to the first and second expandable members 320, 420. As another example, the one or more internal cavities or channels may be provided for washing fluid, positive pressure, and/or negative pressure to be supplied from one or more external pressure sources (not shown) to the first cleansing assembly 338. As another example, the one or more internal cavities or channels may be provided for electrical and/or data cables to extend to the first image capturing assembly 336. As another example, the one or more internal cavities or channels may be provided for cables to extend to one or more sensors (e.g., for haptic feedback, temperature sensor, pressure sensor, etc., not shown), etc. Other internal cavities or channels for other purposes are also contemplated in the present disclosure. It is to be understood that an internal cavity or channel of the first region 310 of the head assembly body 300 may be any cavity or channel (including those that are wholly or partially within the head assembly body 300), and may include a smaller tube, or the like, provided in a larger channel or tube. It is also to be understood that an internal cavity or channel of the first region 310 of the head assembly body 300 may extend beyond the first region 310 of the head assembly body 300. The first region 310 of the head assembly body 300 may have a length between about 12 mm to about 20 mm, and a diameter between about 12 mm to about 20 mm. The first region 310 of the head assembly body 300 may be cylindrical in shape and/or formed having one or more of a plurality of cross-sectional shapes, including a circular cross-section, elliptical cross-section, etc. Other dimensions and shapes are also contemplated without departing from the teachings of the present disclosure.

In example embodiments, the first end 331 of the second region 330 of the head assembly body 300 is secured to the second section of the first region 310 of the head assembly body 300. As will be further described in the present disclosure, the second region 330 includes one or more first pressure ports 332. The second region 330 also includes one or more first insufflation ports 334. The second region 330 also includes one or more first image capturing assemblies 336. The second region 330 also includes one or more first cleansing assemblies 338. The second region 330 also includes one or more internal cavities or channels. For example, the one or more internal cavities or channels may house at least a portion of a second end of the second main body 402 of the second main body assembly 400. The one or more internal cavities or channels may also house the plurality of actuation control members (e.g., cables, wires, tendons, or the like, as described in the present disclosure) that control the second bendable section 410 of the second main body assembly 400. As another example, the one or more internal cavities or channels may be provided to enable negative pressure and/or positive pressure to be supplied from one or more external pressure sources (not shown) to one or more pressure openings 332, 334, 422. As another example, the one or more internal cavities or channels may be provided for positive pressure and/or negative pressure to be supplied from one or more external pressure sources (not shown) to the second expandable member 420. As another example, the one or more internal cavities or channels may be provided for washing fluid, positive pressure, and/or negative pressure to be supplied from one or more external pressure sources (not shown) to the first cleansing assembly 338. As another example, the one or more internal cavities or channels may be provided for electrical and/or data cables to extend to the first image capturing assembly 336. As another example, the one or more internal cavities or channels may be provided for cables to extend to one or more sensors (e.g., for haptic feedback, temperature sensor, pressure sensor, etc., not shown), etc. Other internal cavities or channels for other purposes are also contemplated in the present disclosure. It is to be understood that an internal cavity or channel of the second region 330 of the head assembly body 300 may be any cavity or channel (including those that are wholly or partially within the head assembly body 300), and may include a smaller tube, or the like, provided in a larger channel or tube. It is also to be understood that an internal cavity or channel of the second region 330 of the head assembly body 300 may extend beyond the second region 330 of the head assembly body 300. The second region 330 of the head assembly body 300 may have a length between about 14 mm to about 25 mm. The second region 330 of the head assembly body 300 may be semi-cylindrical in shape and/or formed having one or more of a plurality of cross-sectional shapes, including a semi-circular cross-section, semi-elliptical cross-section, etc. Other dimensions and shapes are also contemplated without departing from the teachings of the present disclosure.

The First Expandable Member (e.g., First Expandable Member 320).

Figure 4C:
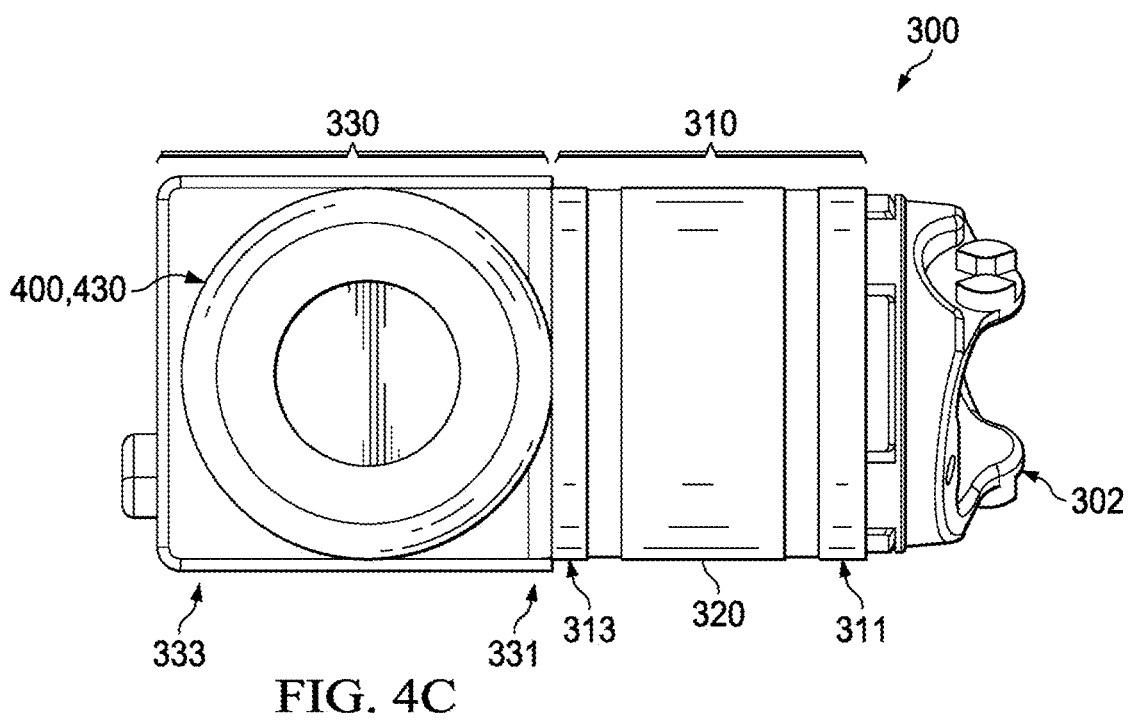
FIG. 4C is a side view illustration of an example embodiment of a head assembly with first expandable member not expanded.
Figure 4D:
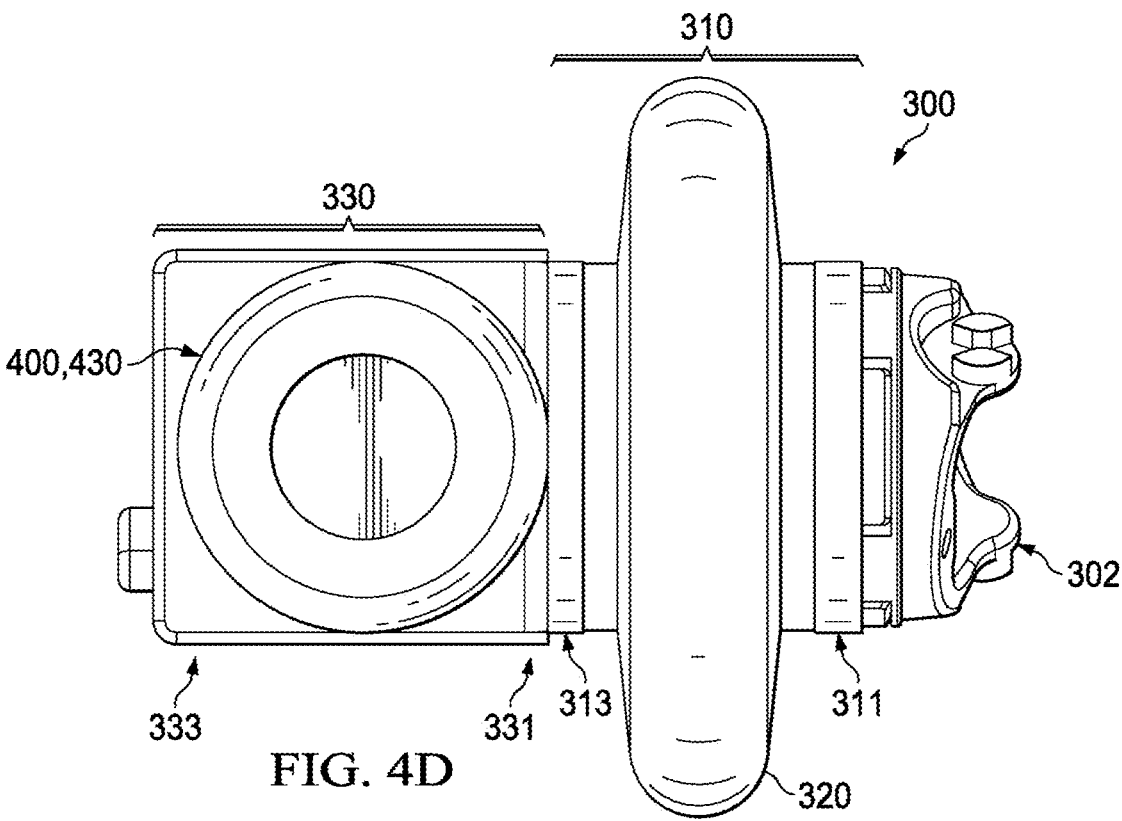
FIG. 4D is a side view illustration of an example embodiment of a head assembly with first expandable member expanded.

As illustrated in at least FIGS. 2 and 4A-D, the head assembly 300 includes one or more first expandable members (e.g., first expandable member 320). As illustrated in at least FIG. 4C, the first expandable member 320 is secured to at least a portion of the first region 310 of the head assembly 300. More specifically, the first expandable member 320 is secured to an exterior portion of the head assembly body 300 between the first and second ends 311, 313 of the first region 310 of the head assembly body 300. The first expandable member 320 is configured to transition between a normal or unexpanded configuration (e.g., as illustrated in FIG. 4C) and an expanded configuration (e.g., as illustrated in FIG.

4D) in which the first expandable member 320 expands radially outward or away from the head assembly body 300.

When the first expandable member 320 is controlled to be in the expanded configuration while in a cavity of a patient, the controller (not shown) is configured to control the first expandable member 320 to expand radially outward or away from the head assembly body 300 towards and/or to the cavity wall of the patient. When expanded, the first expandable member 320 may or may not reach the cavity wall of the patient. In situations where the first expandable member 320 (when expanded) reaches the cavity wall of the patient, the first expandable member 320 may encourage or push outward the cavity wall of the patient. However, in example embodiments, the first expandable member (when expanded) may stop just short (may not reach) or may not push outward (if it reaches) the cavity wall of the patient. In either of these situations, it is recognized that the first expandable member 320 in cooperation (or in combination) with one or more of the first pressure ports 332 (as further described in the present disclosure, which is configured to encourage, bring in, suction inward, and/or collapse a portion of the cavity wall of the patient) enables the system 100 to anchor, grip, and/or otherwise secure to the cavity wall of the patient.

The first expandable member 320 may be formed completely or partially around the first region 310 of the head assembly body 300. The first expandable member 320 may resemble a balloon, or the like, and may include one or more openings (not shown) to allow positive pressure (e.g., passage of gas and/or liquid, and/or allow a manipulation of pressure within the first expandable member 320) to be introduced, controlled, and/or reduced in the first expandable member 320. Each such opening may be connected to one or more of the pressure cavities, which are in turn connected to one or more external pressure sources (not shown). Alternatively, the first expandable member 320 may be formed via one or more membranes (e.g., rectangular sheets) of expandable material, and the opposing long sides of such membranes may be secured (e.g., via an overmolding process) to the first and second ends 311, 313 of the first region 310 of the head assembly body 300.

When in the expanded configuration, which may be a state in which the external pressure source provides a positive pressure to the first expandable member 320, the first expandable member 320 may be configurable to expand radially outward (e.g., resembling a balloon, tire, or the like) with an overall diameter of the first expandable member 320, when in the expanded configuration, between about 25 mm to 40 mm. Other dimensions are also contemplated without departing from the teachings of the present disclosure.

The First Pressure Port (e.g. First Pressure Port 332).

As illustrated in at least FIGS. 2 and 4A-B, the head assembly 300 includes one or more first pressure ports (e.g., first pressure port 332; also referred to herein as the "first pressure opening" 332). The one or more first pressure ports 332 may be provided at the second end 333 of the second region 330, and configured to provide negative pressure (and/or positive pressure) to an exterior of the head assembly body 300 (e.g., to a cavity of a patient). For example, as illustrated in at least FIG. 4A, the one or more first pressure ports 332 may be provided on (or through) the head assembly body 300 at a most distal wall or face of the head assembly body 300 in such a way that a negative pressure applied by the one or more first pressure ports 332 is directed in a direction in which the head assembly body 300 is pointed (or advanced) (e.g., parallel to a central axis formed through the head assembly body 300). Alternatively or in addition, in example embodiments in which the one or more first pressure ports 332 are provided on (or through) the most distal wall or face of the head assembly body 300, one or more of the first pressure ports 332 may be oriented, configured, directed, or pointed in such a way that a negative pressure applied by such one or more first pressure ports 332 is directed in a direction that is not parallel to a central axis formed through the head assembly body 300 (e.g., 10-80 degrees from the central axis formed through the head assembly body 300). Alternatively or in addition, in example embodiments where more than one first pressure ports 332 are provided on (or through) the head assembly body 300, such first pressure ports 332 may be provided around a circumference of the head assembly body 300 (e.g., if a portion of the head assembly body 300 has a circular circumference, such as the first region 310; or otherwise distributed around the head assembly body 300). Alternatively or in addition, in example embodiments where more than one first pressure port 332 is provided on (or through) the head assembly body 300, such first pressure ports 330 may be provided at one or more different locations along the head assembly body 300 (e.g., in the first region 310 and/or the second region 330). The one or more first pressure openings 332 may be configured to provide a negative pressure so as to encourage, bring in, suction inward, and/or collapse a portion of cavity wall of a patient toward the head assembly body 300. It is recognized in the present disclosure that such encouraging, bringing in, suctioning inward, and/or collapsing of a portion of the cavity wall of the patient in combination with an expansion radially outward of the first expandable member 320 towards and/or to a portion of the cavity wall of the patient enables the system 100 to anchor, grip, and/or otherwise secure to the cavity wall of the patient.

Although the Figures illustrate that the first pressure port 332 is provided at the second end 333 of the second region 330 of the head assembly body 300, it is to be understood that other configurations are also contemplated in the present disclosure. For example, in addition to or in replacement of the one or more first pressure ports 332 provided at the second end 333 of the second region 330, the one or more first pressure ports 332 may be provided on a side portion (e.g., between the first and second ends 331, 333) of the second region 330 of the head assembly body 300. Alternatively or in addition, the one or more first pressure ports 332 may be provided at the second end 313 of the first region 310 of the head assembly body 300. Alternatively or in addition, the one or more first pressure ports 332 may be provided at the first end 311 of the first region 310 of the head assembly body 300.

The First Insufflation Port (e.g., First Insufflation Port 334).

As illustrated in at least FIGS. 2 and 4A-B, the head assembly 300 includes one or more first insufflation ports (e.g., first insufflation port 334; also referred to herein as the "first insufflation opening" 334). The one or more first insufflation ports 334 may be provided at the second end 333 of the second region 330, and configured to provide positive pressure to an exterior of the head assembly body 300 (e.g., to a cavity of a patient to insufflate the cavity of the patient). For example, the one or more first insufflation openings 334 may be configured to provide a positive pressure so as to encourage, push outward, and/or expand a portion of cavity wall of a patient away from the head assembly body 300.

Although the Figures illustrate that the first insufflation port 334 is provided at the second end 333 of the second region 330 of the head assembly body 300, it is to be understood that other configurations are also contemplated in the present disclosure. For example, in addition to or in replacement of the one or more first insufflation ports 334 provided at the second end 333 of the second region 330, the one or more first insufflation ports 334 may be provided on a side portion (e.g., between the first and second ends 331, 333) of the second region 330 of the head assembly body 300. Alternatively or in addition, the one or more first insufflation ports 334 may be provided at the second end 313 of the first region 310 of the head assembly body 300. Alternatively or in addition, the one or more first insufflation ports 334 may be provided at the first end 311 of the first region 310 of the head assembly body 300.

The First Image Capturing Assembly (e.g., First Image Capturing Assembly 336).

As illustrated in at least FIGS. 2 and 4A-B, the head assembly 300 includes one or more first image capturing assemblies (e.g., first image capturing assembly 336). The first image capturing assembly 336 may be any image and/or video capturing device including, but not limited to, a 2-D video camera and/or a 3-D stereoscopic or autostereoscopic video camera. The first image capturing assembly 336 may also include one or more illumination sources (not shown), or the like, such as one or more LED lights.

Although the Figures illustrate that the first image capturing assembly 336 is provided at the second end 333 of the second region 330 of the head assembly body 300, it is to be understood that other configurations are also contemplated in the present disclosure. For example, in addition to or in replacement of the one or more first image capturing assemblies 336 provided at the second end 333 of the second region 330, the one or more first image capturing assemblies 336 may be provided on a side portion (e.g., between the first and second ends 331, 333) of the second region 330 of the head assembly body 300. Alternatively or in addition, the one or more first image capturing assemblies 336 may be provided at the second end 313 of the first region 310 of the head assembly body 300. Alternatively or in addition, the one or more first image capturing assemblies 336 may be provided at the first end 311 of the first region 310 of the head assembly body 300.

The First Cleansing Assembly (e.g., First Cleansing Assembly 338).

As illustrated in at least FIGS. 2 and 4A-B, the head assembly 300 includes one or more first image cleansing assemblies (e.g., first cleansing assembly 338). The first cleansing assembly 338 may be configured to direct a fluid (e.g., water, non-toxic washing fluid, etc.), positive pressure, and/or negative pressure to the first image capturing assembly 336 so as to clean, unblock, and/or otherwise improve visibility and/or image capturing quality of the first image capturing assembly 336.

Although the Figures illustrate that the first cleansing assembly 338 is provided at the second end 333 of the second region 330 of the head assembly body 300, it is to be understood that other configurations are also contemplated in the present disclosure (so long as it is nearby the first image capturing assembly 336). For example, in addition to or in replacement of the one or more first cleansing assembly 338 provided at the second end 333 of the second region 330, the one or more first cleansing assembly 338 may be provided on a side portion (e.g., between the first and second ends 331, 333) of the second region 330 of the head assembly body 300. Alternatively or in addition, the one or more first cleansing assembly 338 may be provided at the second end 313 of the first region 310 of the head assembly body 300. Alternatively or in addition, the one or more first cleansing assembly 338 may be provided at the first end 311 of the first region 310 of the head assembly body 300.

The Second Main Body Assembly (e.g., Second Main Body Assembly 400).

As illustrated in at least FIG. 2 and FIGS. 4E-I, each system 200 includes a second main body assembly 200. The second main body assembly 400 includes one or more elements. For example, the second main body assembly 400 includes a second main body 402. The second main body assembly 400 also includes a second bendable section 410. The second main body assembly 400 also includes one or more second expandable members 420. The second main body assembly 400 also includes one or more second pressure openings 422. The second main body assembly 400 also includes a magnetic implant assembly 430. The second main body assembly 400 also includes a securing assembly 440.

These and other elements of the second main body assembly 400 will now be described with reference to the accompanying figures.

The Second Main Body (e.g., Second Main Body 402).

As illustrated in at least FIGS. 4E-I, an example embodiment of the second main body assembly 400 includes a second main body 402. The second main body 402 may include an elongated tubular structure, or the like, having a first end (or "proximal end") and a second end (or "distal end", which is the end nearest and/or secured to the securing assembly 440). The second main body 402 may include a flexible body having one or more internal channels (not shown). For example, the one or more internal channels may be provided for the plurality of actuation control members (e.g., cables, wires, tendons, or the like) to extend from the controller and/or surgeon console to a portion of the second end of the second main body 402. As another example, the one or more internal channels may be provided to enable negative pressure and/or positive pressure to be supplied from one or more external pressure sources (not shown) to the one or more second pressure openings 422. As another example, the one or more internal channels may be provided for positive pressure and/or negative pressure to be supplied from one or more external pressure sources (not shown) to the second expandable member 420. As another example, the one or more internal channels may be provided for cables to control the securing assembly 440 (e.g., control the securing and unsecuring of the magnetic implant assembly 430). Other internal channels for other purposes are also contemplated in the present disclosure. It is to be understood that an internal channel of the second main body 402 may be any channel (including those that are wholly or partially within the first main body assembly), and may include a smaller tube, or the like, provided in a larger channel or tube. It is also to be understood that an internal channel of the second main body 402 may extend beyond the first end and/or second end of the second main body 402.

As illustrated in at least FIGS. 4E-I, the second end of the second main body 402 may be securable or secured to (and in example embodiments, detachable from) the securing assembly 440. The second end of the second main body 402 may also be securable or secured to (and in example embodiments, detachable from) the magnetic implant assembly 430 (e.g., via the securing assembly 440).

In an example embodiment, the second main body 400 may have a length between about 1800 mm to about 2500 mm, and a diameter between about 2 mm to about 4 mm. The second main body 400 may be formed having one or more of a plurality of cross-sectional shapes, including a circular cross-section, elliptical cross-section, etc. Other dimensions and shapes are also contemplated without departing from the teachings of the present disclosure.

The Second Bendable Section (e.g., Second Bendable Section 410).

Figures 4E, 4F:
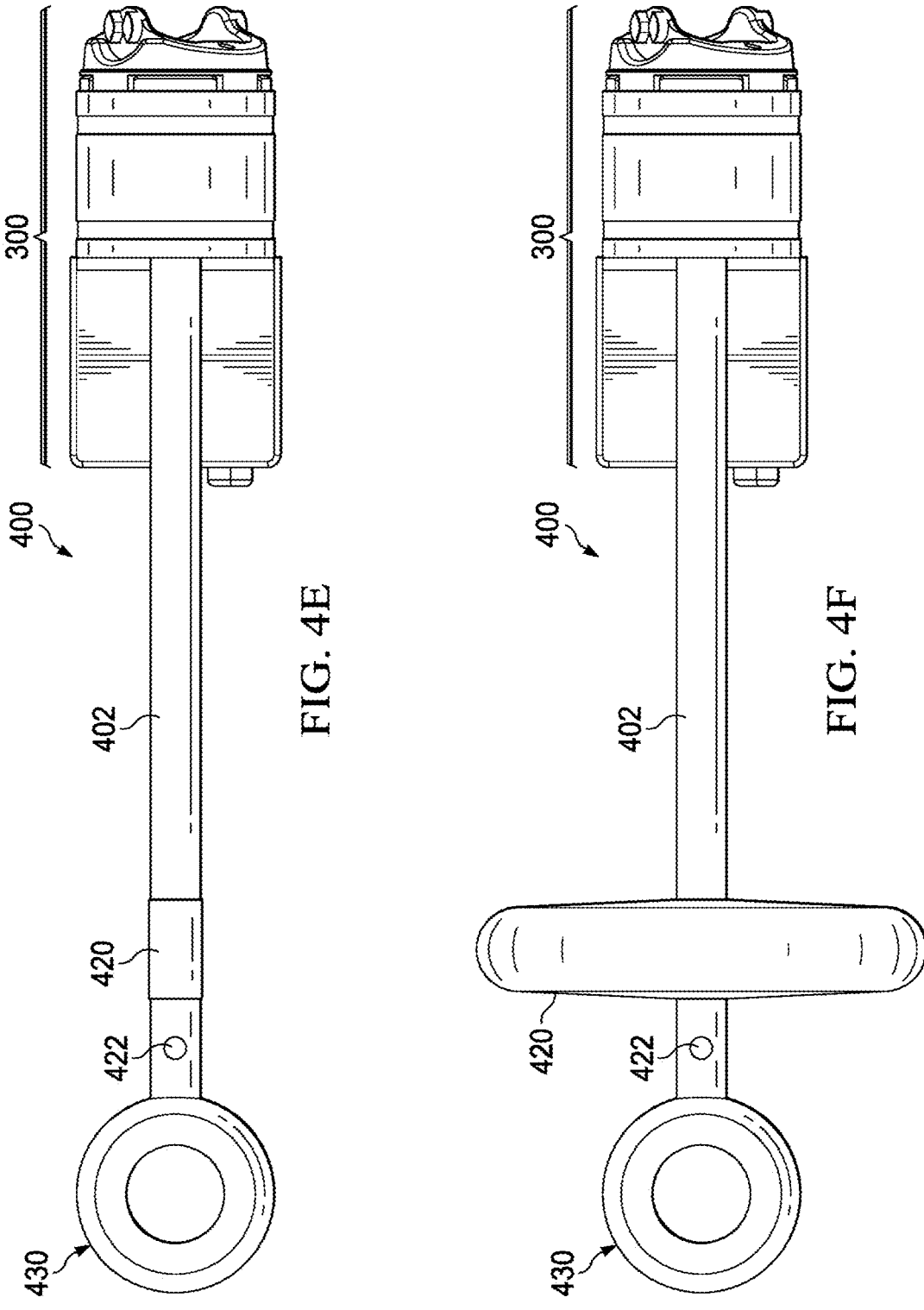
FIG. 4E is a side view illustration of an example embodiment of a second main body assembly extended outward away from a head assembly.
FIG. 4F is a side view illustration of an example embodiment of a second main body assembly extended outward away from a head assembly, and a first expandable member configured to expand.
Figures 4G, 4H:
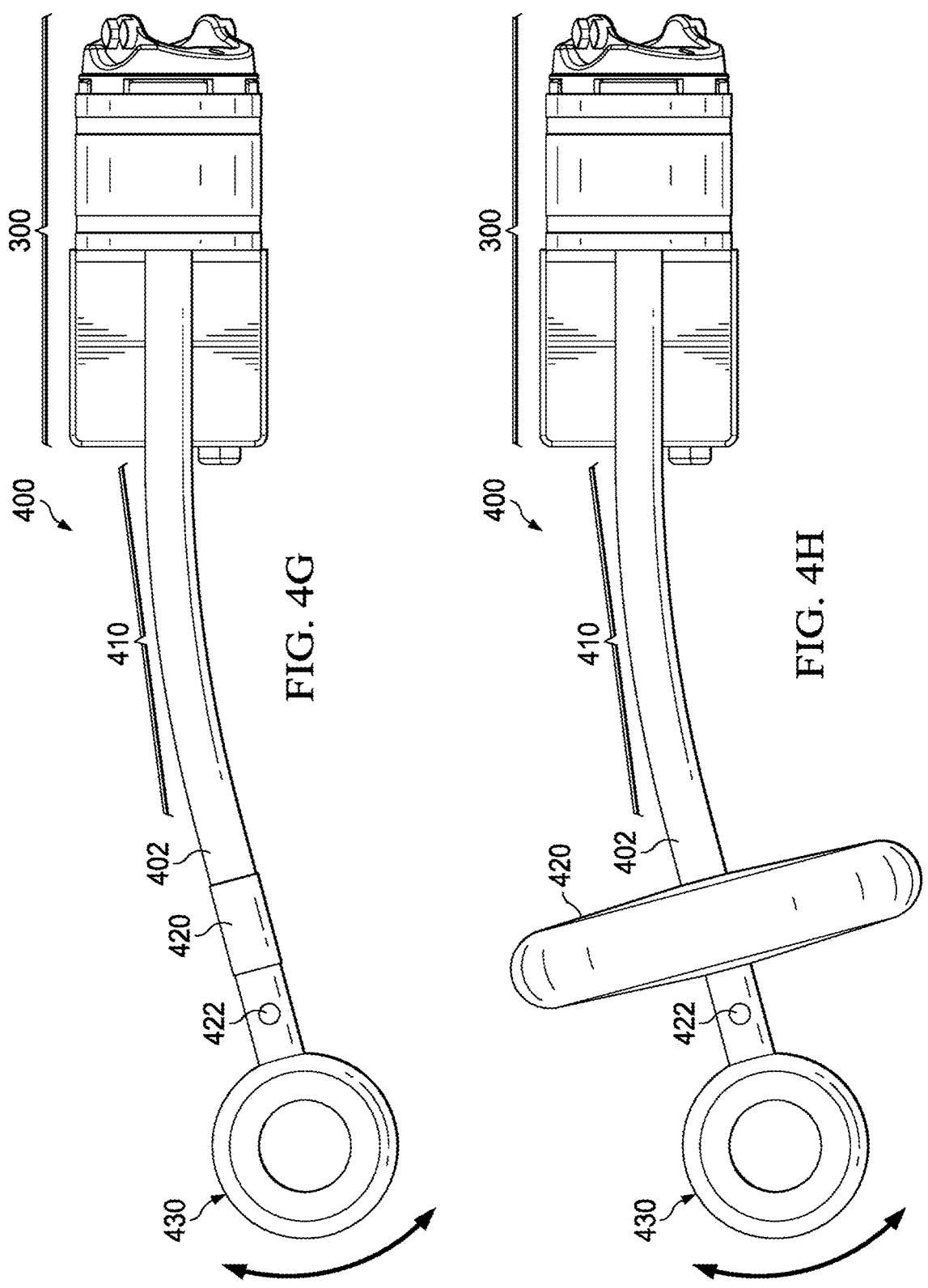
FIG. 4G is a side view illustration of an example embodiment of a second main body assembly extended outward away from a head assembly, and a second bendable section configured to bend.
FIG. 4H is a side view illustration of an example embodiment of a second main body assembly extended outward away from a head assembly, a second bendable section configured to bend, and a second expandable member configured to expand.

As illustrated in at least FIG. 4G and FIG. 4H, the second main body assembly 400 includes one or more second bendable sections (e.g., second bendable section 410). The one or more second bendable sections 410 may be provided at the second end of the second main body assembly 400.

In an example embodiment, the second bendable section 410 is configurable or configured to bend the second main body assembly 400 in any one or more of a plurality of available directions and/or one or more of a plurality of locations along the second bendable section 410. This may be desirable when the second main body assembly 400 is being advanced forward into a body cavity, such as a colon or small bowel, and the system 100 reaches a bend, turn, or the like in the body cavity. Alternatively or in addition, such bending may be desirable when a particular area of the interior wall of the body cavity needs to be viewed and/or actioned (e.g., delivering of the magnetic implant body 430). Such bending of the second bendable section 410 may be achievable or achieved by selectively configuring one or more locations along the second bendable section 410 to bend (e.g., away from a center axis formed by the second bendable section 410). Such selective configuring may include selecting one or more locations along the second bendable section 410 to bend from among a plurality of bendable location(s) along the second bendable section 410. FIGS. 4G-H illustrate an example of bending of the second bendable section 410. Selective configuring may also include selecting, for each location along the second bendable section 410, a degree of curvature for the bending from among a plurality of available degrees of curvature. Selective configuring may also include selecting, for each location along the second bendable section 410, one or more directions for the bending from among a plurality of available directions, etc.

The bending of the second bendable section 410 may be selectively controllable by controlling an amount of force (e.g., tension via pulling or pushing) applied (increased, decreased, maintained, or not applied) to one or more actuation control members (not shown) and/or selecting one or more of the actuation control members to selectively control (i.e., which actuation control member will receive an increase in applied force, decrease in applied force, no change in applied force, and/or no applied force). In an example embodiment, the second bendable section 410 may include a serially (or linearly) connected arrangement of a plurality of bendable subsections (not shown). Each bendable subsection may include one or more distal termination points for receiving, securing, terminating, and/or connecting one or more actuation control members.

Each of the bendable subsections may include one or more internal cavities or channels for, among other things, enabling one or more actuation control members to extend through, enabling negative pressure and/or positive pressure to be provided to the one or more pressure openings 422, enabling positive pressure and/or negative pressure to be provided to the second expandable member 420, enabling cables to extend to the securing assembly 440, etc.

The distal termination points for the one or more actuation control members may be provided in any shape or form so long as it enables the receiving, connecting, terminating, and/or securing of the distal end of one or more actuation control members. For example, the distal termination point may be an opening, connector, termination, hook, etc. A degree of bending of one or more of the bendable locations of the second bendable section 410 may be between about 0 to 210 degrees from a center axis in example embodiments.

In an example embodiment, a length of the second bendable section 410 may be between about 5 mm to about 50 mm, and a diameter of the second bendable section 410 may be between about 2 mm to about 4 mm in example embodiments. Other dimensions are also contemplated without departing from the teachings of the present disclosure.

Although the Figures illustrate that the sequence or order of the elements (e.g., when moving towards the securing assembly 440 or the magnetic implant assembly 430) are such that the second expandable member 420 is provided between the second bendable section 410 and the one or more second pressure ports 422, it is to be understood that other configurations are also contemplated in the present disclosure. For example, the one or more second pressure ports 422 may be provided between the second bendable section 410 and the second expandable member 420. As another example, the bendable section 410 may be provided between the second expandable member 420 and the one or more second pressure ports 422. The sequence or order of the elements may also be changed from the sequence shown in the Figures (which illustrates a sequence of the second bendable section 410, followed by the second expandable member 420, followed by the one or more second pressure ports 422). For example, the sequence may be the one or more second pressure ports 422, followed by the second expandable member 420, followed by the second bendable portion 410. As another example, the sequence may be the one or more second pressure ports 422, followed by the second bendable portion 410, followed by the second expandable member 420. As another example, the sequence may be the second expandable member 420, followed by the one or more second pressure ports 422, followed by the second bendable portion 410. As another example, the sequence may be the second expandable member 420, followed by the second bendable portion 410, followed by the one or more second pressure ports 422.

Figures 4I, 5A, 5B:
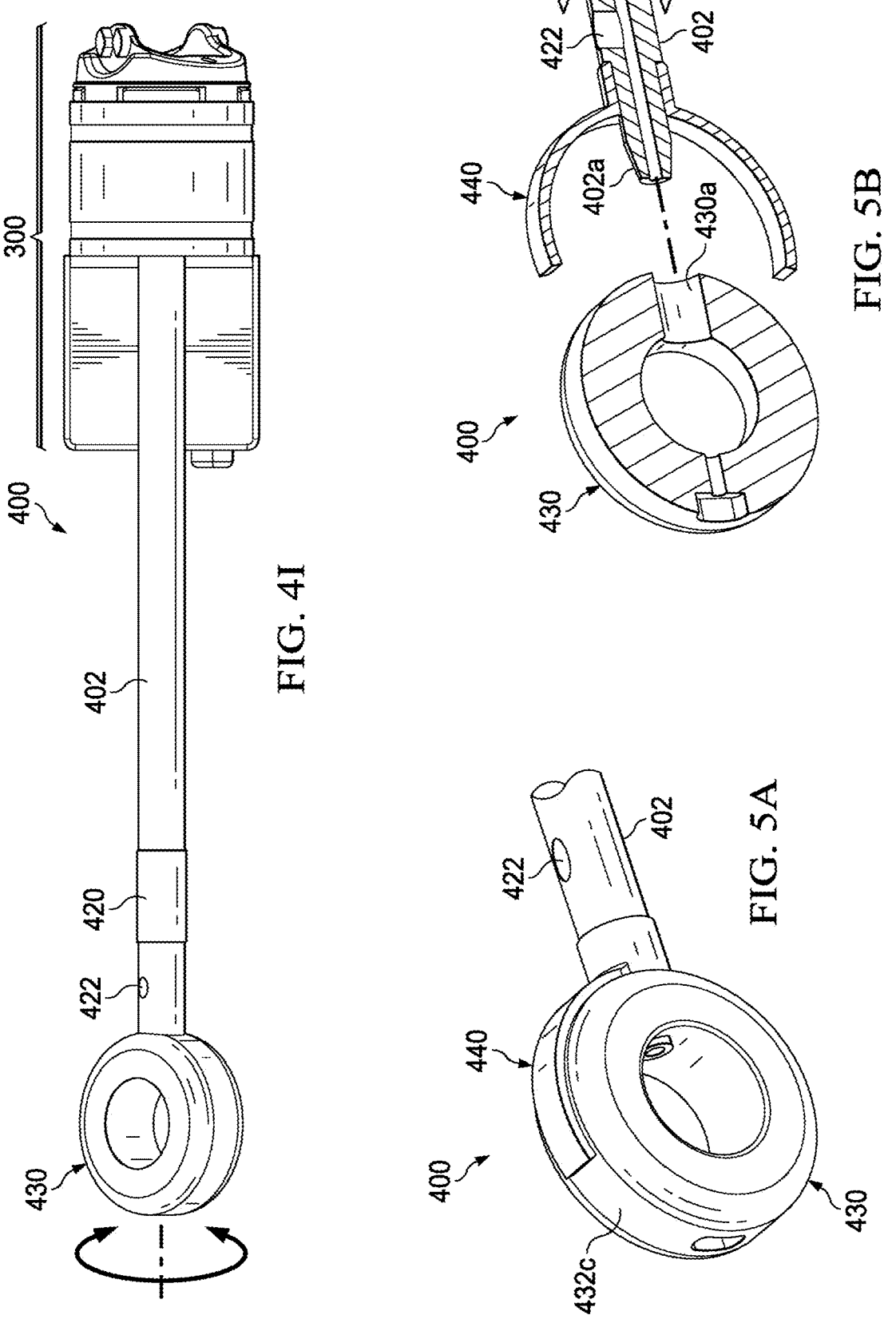
FIG. 4I is a side view illustration of an example embodiment of a second main body assembly extended outward away from a head assembly and rotated so as to change an orientation of a magnetic implant assembly.
FIG. 5A is a perspective view illustration of an example embodiment of a magnetic implant assembly secured to a second main body assembly via a securing assembly.
FIG. 5B is a cross-sectional view illustration of an example embodiment of a magnetic implant assembly, a securing assembly, and a second main body assembly.

As illustrated in FIG. 4I, an example embodiment of the second main body assembly 400 is also configurable or configured to rotate relative to a central axis formed by the second main body 402. Such rotation enables an orientation of the magnetic implant assembly 430 to be selectively change, which, along with the bending of the second bendable section 410, can assist with the positioning of the magnetic implant assembly 430 for magnetically coupling to another magnetic implant assembly 430'.

The Second Expandable Member (e.g., Second Expandable Member 420).

As illustrated in at least FIGS. 2 and FIGS. 4E-I, the second main body assembly 400 includes one or more second expandable members (e.g., second expandable member 420). As illustrated in at least FIG. 4E, the second expandable member 420 is secured to a portion of the second end of the second main body assembly 400. The second expandable member 420 is configured to transition between a normal or unexpanded configuration (e.g., as illustrated in FIG. 4E) and an expanded configuration (e.g., as illustrated in FIG. 4F and FIG. 4H) in which the second expandable member 420 is expanded radially outward or away from the second main body 402 (or towards or to a cavity wall of the patient).

When the second expandable member 420 is controlled to be in the expanded configuration while in a cavity of a patient, the controller (not shown) is configured to control the second expandable member 420 to expand radially outward or away from the second main body 402 and towards and/or to the cavity wall of the patient. When expanded, the second expandable member 420 may or may not reach the cavity wall of the patient. In situations where the second expandable member 420 (when expanded) reaches the cavity wall of the patient, the second expandable member 420 may encourage or push outward the cavity wall of the patient. However, in example embodiments, the second expandable member 420 (when expanded) may stop just short (may not reach) or may not push outward (if it reaches) the cavity wall of the patient. In either of these situations, it is recognized that the second expandable member 420 in cooperation (or in combination) with one or more of the second pressure ports 422 (as further described in the present disclosure, which is configured to encourage, bring in, suction inward, and/or collapse a portion of the cavity wall of the patient) enables the system 100 to anchor, grip, and/or otherwise secure to the cavity wall of the patient.

The second expandable member 420 may be formed completely or partially around the second main body 402. The second expandable member 420 may resemble a balloon, or the like, and may include one or more openings (not shown) to allow positive pressure (e.g., passage of gas and/or liquid, and/or allow a manipulation of pressure within the second expandable member 420) to be introduced, controlled, and/or reduced in the second expandable member 420. Each such opening may be connected to one or more of the pressure cavities, which are in turn connected to one or more external pressure sources (not shown). Alternatively, the second expandable member 420 may be formed via one or more membranes (e.g., rectangular sheets) of expandable material, and the opposing long sides of such membranes may be secured (e.g., via an overmolding process) cicumferentially around the second main body 402.

When in the expanded configuration, which may be a state in which the external pressure source provides a positive pressure to the second expandable member 420, the second expandable member 420 may be configurable to expand radially outward (e.g., resembling a balloon, tire, or the like) with an overall diameter of the second expandable member 420, when in the expanded configuration, between about 10 mm to 30 mm. Other dimensions are also contemplated without departing from the teachings of the present disclosure.

Although the Figures illustrate that the sequence or order of the elements (e.g., when moving towards the securing assembly 440 or the magnetic implant assembly 430) are such that the second expandable member 420 is provided between the second bendable section 410 and the one or more second pressure ports 422, it is to be understood that other configurations are also contemplated in the present disclosure. For example, the one or more second pressure ports 422 may be provided between the second bendable section 410 and the second expandable member 420. As another example, the bendable section 410 may be provided between the second expandable member 420 and the one or more second pressure ports 422. The sequence or order of the elements may also be changed from the sequence shown in the Figures (which illustrates a sequence of the second bendable section 410, followed by the second expandable member 420, followed by the one or more second pressure ports 422). For example, the sequence may be the one or more second pressure ports 422, followed by the second expandable member 420, followed by the second bendable portion 410. As another example, the sequence may be the one or more second pressure ports 422, followed by the second bendable portion 410, followed by the second expandable member 420. As another example, the sequence may be the second expandable member 420, followed by the one or more second pressure ports 422, followed by the second bendable portion 410. As another example, the sequence may be the second expandable member 420, followed by the second bendable portion 410, followed by the one or more second pressure ports 422.

The Second Pressure Port (e.g., Second Pressure Port 422).

As illustrated in at least FIGS. 2 and 4E-I, the second main body assembly 400 includes one or more second pressure ports (e.g., second pressure port 422; also referred to herein as the "second pressure opening" 422). The one or more second pressure ports 422 may be provided at the second end of the second main body assembly 400, and configured to provide negative pressure (and/or positive pressure) to an exterior of the second main body 402 (e.g., to a cavity of a patient). In example embodiments where more than one second pressure ports 422 are provided on (or through) the second main body 402, such second pressure ports 422 may be provided around a circumference of the second main body 402 (e.g., if the second main body 402 has a circular circumference; or otherwise around the head assembly body 300). Alternatively or in addition, in example embodiments where more than one second pressure port 422 is provided on (or through) the second main body 402, such second pressure ports 422 may be provided at one or more different locations along the second main body 402. For example, as illustrated in at least FIG. 4E, one or more second pressure ports 422 may be provided on (or through) the second main body 402 at a location between the securing assembly 440 (or most distal part of the second main body 402) and the second expandable member 420 (or most distal second expandable member 420 if there are more than one second expandable members 420). As another example (not shown), one or more second pressure ports 422 may be provided on (or through) the second main body 402 in such a way that the second expandable member 420 is provided between the one or more second pressure ports 422 and the securing assembly 440 (or most distal part of the second main body 402). As another example (not shown), one or more second pressure ports 422 may be provided on (or through) the second main body 402 before and after (or distal and proximal to) the second expandable member 420. As another example (not shown), in example embodiments in which there are two or more second expandable members 420 secured to the second main body 402, a plurality of second pressure ports 422 may be provided on (or through) the second main body 402 in such a way that second pressure ports 422 are provided before and after (or distal and proximal to) each of the second expandable members 420. The one or more second pressure ports 422 may be configured to provide a negative pressure so as to encourage, bring in, suction inward, and/or collapse a portion of cavity wall of a patient toward the second main body 402. It is recognized in the present disclosure that such encouraging, bringing in, suctioning inward, and/or collapsing of a portion of the cavity wall of the patient in combination with an expansion radially outward of the one or more second expandable members 420 towards and/or to a portion of the cavity wall of the patient enables the second main body assembly 400 to anchor, grip, and/or otherwise secure to the cavity wall of the patient.

Although the Figures illustrate that the sequence or order of the elements (e.g., when moving towards the securing assembly 440 or the magnetic implant assembly 430) are such that the second expandable member 420 is provided between the second bendable section 410 and the one or more second pressure ports 422, it is to be understood that other configurations are also contemplated in the present disclosure. For example, alternatively or in addition, the one or more second pressure ports 422 may be provided between the second bendable section 410 and the second expandable member 420. As another example, alternatively or in addition, the bendable section 410 may be provided between the second expandable member 420 and the one or more second pressure ports 422. The sequence or order of the elements may also be changed from the sequence shown in the Figures (which illustrates a sequence of the second bendable section 410, followed by the second expandable member 420, followed by the one or more second pressure ports 422). For example, the sequence may be the one or more second pressure ports 422, followed by the second expandable member 420, followed by the second bendable portion 410. As another example, the sequence may be the one or more second pressure ports 422, followed by the second bendable portion 410, followed by the second expandable member 420. As another example, the sequence may be the second expandable member 420, followed by the one or more second pressure ports 422, followed by the second bendable portion 410. As another example, the sequence may be the second expandable member 420, followed by the second bendable portion 410, followed by the one or more second pressure ports 422.

The Magnetic Implant Assembly (e.g., Magnetic Implant Assembly 430).

As illustrated in at least FIGS. 2 and 4E-I, the second main body assembly 400 includes a magnetic implant assembly (e.g., magnetic implant assembly 430, magnetic implant body 430, magnetic body 430, or the like). The magnetic implant assembly 430 is securable to and unsecurable from the second main body 402 via the securing assembly 440. As will be further described in the present disclosure, the magnetic implant assembly 430 may be formed, in whole or in part, as or using ferromagnetic or magnetic materials.

The magnetic implant assembly 430 may be configured in one or more configurations. In this regard, an example embodiment of a first magnetic implant assembly 430 of one system 100 (e.g., a first system 100 for delivering of the magnetic implant assembly 430 orally via entry through a mouth of the patient) may or may not be the same as an example embodiment of a second magnetic implant assembly 430 of another system 100 (e.g., a second system 100 for delivering of the magnetic implant assembly 430 rectally via entry through the rectum of the patient). For example, as illustrated in FIGS. 6A, 6B, 7A, and 7B and as will be further described in the present disclosure, the second magnetic implant assembly 430' may not include any protrusions 434 and/or indentations 435 and the first magnetic implant assembly 430 may include one or more protrusions 434 and/or one or more indentations 435.

Example embodiments of the magnetic implant assembly 430 will now be described with reference to FIGS. 6A-D and 7A-D.

First Example Embodiment of the Magnetic Implant Assembly 430

As illustrated in the cross-sectional side views of FIG. 6A and FIG. 6B and the top views of FIG. 6C and FIG. 6D, a first magnetic implant assembly 430 may be formed as and/or include a flat and cylindrical body 432 (e.g., flat when viewed from the side and circular when viewed from the top). The body 432 is formed, in whole or in part, as or using a ferromagnetic or magnetic material.

The first magnetic implant assembly 430 includes a front wall 432a (e.g., the lower wall 432a of the upper magnetic implant assembly 430 illustrated in FIGS. 6A and 6B; the wall 432a illustrated in FIGS. 6C and 6D). In example embodiments, the front wall 432a is the wall that will be magnetically coupled to or facing the second magnetic implant assembly 430'. The front wall 432a may have a circular shape with a central axis formed through the center of the front wall 432a. The front wall 432a may have a radius of R1 (from the central axis), as illustrated in FIGS. 6C-D. In an example embodiment, the first magnetic implant assembly 430 may also include a hole, bore, or the like, through the center axis, as illustrated in at least FIG. 6D. In such embodiments, the hole may have a radius of R4 (from the central axis).

The first magnetic implant assembly 430 includes a rear wall 432b opposite to the front wall 432a. In example embodiments, the rear wall 432b is not the wall that will be magnetically coupled to or facing the second magnetic implant assembly 430'. The rear wall 432b will have substantially the same shape and central axis as the front wall 432a, and radius R1 (from the central axis).

The first magnetic implant assembly 430 includes a first exterior circumferential sidewall 432c formed around the magnetic body 432. The first exterior circumferential sidewall 432c may define a thickness of the magnetic body 432. The first exterior circumferential sidewall 432c may be formed at the radius R1 from the central axis.

In an example embodiment, the first magnetic implant assembly 430 includes one or more protrusions 434 formed on the front wall 432a. The one or more protrusions 434 may be formed in one or more of a plurality of shapes or forms. The one or more protrusions 434 may be formed using ferromagnetic or magnetic material. For example, as illustrated in FIGS. 6A-D, the protrusion 434 may be in the shape of a protruded ring having an exterior radius of R2 and an interior radius of R3. Alternatively or in addition, the first magnetic implant assembly 430 may include another protrusion (not shown) formed on the protrusion that has radiuses R2 and R1 (e.g., in a stepped manner), where the additional protrusion has an exterior radius between R2 and R1. One or more other protrusions may also be formed on the front wall 432a and/or another protrusion 432 without departing from the teachings of the present disclosure. In example embodiments, one or more of the protrusions 434 may not necessarily be formed using the same ferromagnetic or magnetic material (and/or the same magnetic force) as the body 432. For example, one or more of the protrusions 434 may be formed as or using a weaker magnet (or ferromagnetic or magnetic material having a weaker magnetic force) as compared to the ferromagnetic or magnetic material of the body 432. As another example, one or more of the protrusions 434 may be formed as or using a stronger magnet (or ferromagnetic or magnetic material having a stronger magnetic force) as compared to the ferromagnetic or magnetic material of the first magnetic implant assembly 430. As another example, one or more of the protrusions 434 may not be formed using (and/or may not include) a ferromagnetic or magnetic material, and instead may be formed using other materials such as plastic, silicon rubber, etc. Other configurations, magnetic coupling strengths, and/or materials/compositions are also contemplated without departing from the teachings of the present disclosure.

In example embodiments where the first magnetic implant assembly 430 includes a circular or ring-shaped protrusion 434 formed on the front wall 432a, the second magnetic implant assembly 430' may be formed as and/or include a flat and cylindrical body 432' (e.g., flat when viewed from the side and circular when viewed from the top).

The second magnetic implant assembly 430' includes a front wall 432a' (e.g., the upper wall 432a' of the lower magnetic implant assembly 430' illustrated in FIGS. 6A and 6B). In example embodiments, the front wall 432a' is the wall that will be magnetically coupled to or facing the second magnetic implant assembly 430'. The front wall 432a' may have a circular shape with a central axis formed through the center of the front wall 432a'. The front wall 432a' may have a radius equal or not equal to R1 (from the central axis), but larger than radius R2. In an example embodiment, the second magnetic implant assembly 430' may also include a hole, bore, or the like, through the center axis, similar to that of the first magnetic implant assembly 430.

The second magnetic implant assembly 430' includes a rear wall 432b' opposite to the front wall 432a'. In example embodiments, the rear wall 432b' is not the wall that will be magnetically coupled to or facing the first magnetic implant assembly 430. The rear wall 432b' will have substantially the same shape and central axis as the front wall 432a', and radius (from the central axis).

The second magnetic implant assembly 430' includes a second exterior circumferential sidewall 432c' formed around the magnetic body 432'. The second exterior circumferential sidewall 432c' may define a thickness of the magnetic body 432'. The thickness of the magnetic body 432' may or may not be the same as the thickness of the magnetic body 432 of the first magnetic implant assembly 430.

In an example embodiment, the front wall 432a' of the second magnetic implant assembly 430' does not include any protrusions like that of the first magnetic implant assembly 430. It is recognized in the present disclosure that not having protrusions on the front wall 432a' of the second magnetic implant assembly 430' allows for a simple and aligned magnetic coupling with the front wall 432a (i.e., with the protrusions 434) of the first magnetic implant assembly 430 (as illustrated in FIG. 6B). It is to be understood, however, that the front wall 432a' of the second magnetic implant assembly 430' may also include one or more protrusions (not shown) similar to (e.g., different exterior and/or interior radiuses) or the same as (e.g., same exterior and/or interior radiuses) the protrusions 434 of the front wall 432 of the first magnetic implant assembly 430.

It is recognized in the present disclosure that having an exterior portion of the first magnetic implant assembly 430 (i.e., the portion between radius R1 and radius R2) not being magnetically coupled to the second magnetic implant assembly 430' (or being magnetically coupled to the second magnetic implant assembly 430' with a lesser magnetic force due to the airgap between the exterior portion of the first magnetic implant assembly 430 and the second magnetic implant assembly 430') results in a force or pressure (F1) exerted on a first portion of the cavity wall of the patient (i.e., force between the exterior portion of the first magnetic implant assembly 430 between R1 and R2 and the second magnetic implant assembly 430') to be less than a force or pressure (F2) exerted on a second (adjacent) portion of the cavity wall of the patient (i.e., force between the protrusion 434 and the second magnetic implant assembly 430'). In this regard, it is recognized in the present disclosure that the adjacent application of different forces or pressures, as described above and in the present disclosure, improves the healing (and/or enables better controlled healing) of the anastomosis and/or necrosis formed by the first and second magnetic implant assemblies 430, 430'.

It is to be noted in the present disclosure that the first magnetic implant assembly 430 (and/or the second magnetic implant assembly 430') may also include one or more indentations on the front wall 432a (and 432a'). For example, the section of the front wall 432a between the exterior radius R2 and the radius R1 may be an indentation. As another example, the section of the front wall 432a between the interior radius R3 and the central axis (or the radius R4 for the example embodiment illustrated in FIG. 6D) may be an indentation.

Second Example Embodiment of the Magnetic Implant Assembly 430

As illustrated in the cross-sectional side views of FIG. 7A and FIG. 7B and the top views of FIG. 7C and FIG. 7D, a first magnetic implant assembly 430 may be formed as and/or include a flat and cylindrical body 432 (e.g., flat when viewed from the side and circular when viewed from the top). The body 432 is formed, in whole or in part, as or using a ferromagnetic or magnetic material.

The first magnetic implant assembly 430 includes a front wall 432a (e.g., the lower wall 432a of the upper magnetic implant assembly 430 illustrated in FIGS. 7A and 7B; the wall 432a illustrated in FIGS. 7C and 7D). In example embodiments, the front wall 432a is the wall that will be magnetically coupled to or facing the second magnetic implant assembly 430'. The front wall 432a may have a circular shape with a central axis formed through the center of the front wall 432a. The front wall 432a may have a radius of R2 (from the central axis), as illustrated in FIGS. 7C-D. In an example embodiment, the first magnetic implant assembly 430 may also include a hole, bore, or the like, through the center axis, as illustrated in at least FIG. 7D. In such embodiments, the hole may have a radius of R4 (from the central axis).

The first magnetic implant assembly 430 includes a rear wall 432b opposite to the front wall 432a. In example embodiments, the rear wall 432b is not the wall that will be magnetically coupled to or facing the second magnetic implant assembly 430'. The rear wall 432b will have substantially the same shape and central axis as the front wall 432a, and radius R1 (from the central axis).

The first magnetic implant assembly 430 includes a first exterior circumferential sidewall 432c formed around the magnetic body 432. The first exterior circumferential sidewall 432c may define a thickness of the magnetic body 432 (and protrusion 434, as further described below). The first exterior circumferential sidewall 432c may be formed at the radius R2 from the central axis.

In an example embodiment, the first magnetic implant assembly 430 includes one or more protrusions 434 formed on the front wall 432a. The one or more protrusions 434 may be formed in one or more of a plurality of shapes or forms. The one or more protrusions 434 may be formed using ferromagnetic or magnetic material. For example, as illustrated in FIGS. 7A-D, the protrusion 434 may be in the shape of a protruded ring having an exterior radius of R2 and an interior radius of R3. One or more other protrusions may also be formed on the front wall 432a without departing from the teachings of the present disclosure. In example embodiments, one or more of the protrusions 434 may not necessarily be formed using the same ferromagnetic or magnetic material (and/or the same magnetic force) as the body 432. For example, one or more of the protrusions 434 may be formed as or using a weaker magnet (or ferromagnetic or magnetic material having a weaker magnetic force) as compared to the ferromagnetic or magnetic material of the body 432. As another example, one or more of the protrusions 434 may be formed as or using a stronger magnet (or ferromagnetic or magnetic material having a stronger magnetic force) as compared to the ferromagnetic or magnetic material of the first magnetic implant assembly 430. As another example, one or more of the protrusions 434 may not be formed using (and/or may not include) a ferromagnetic or magnetic material, and instead may be formed using other materials such as plastic, silicon rubber, etc. Other configurations, magnetic coupling strengths, and/or materials/compositions are also contemplated without departing from the teachings of the present disclosure.

As illustrated in FIGS. 7A-B, the first magnetic implant assembly 430 includes an exterior cylindrical or ring-shaped body 436. The exterior body 436 is formed around and fixedly secured to the first exterior circumferential sidewall 432c of the magnetic body 432. The exterior body 436 includes a front exterior cylindrical or ring-shaped portion, at least a portion of which is adjacent to the front wall 432a. The exterior body 436 may also include a rear exterior cylindrical or ring-shaped portion adjacent to the rear wall 432b. In an example embodiment, the exterior body 436 may or may not be a wholly or fully magnetic body and/or may or may not be magnetically coupled to the second magnetic implant assembly 430' when the first magnetic implant assembly 430 is magnetically coupled to the second magnetic implant assembly 430'. For example, the exterior body 436 may not be formed using (and/or may not include) a ferromagnetic or magnetic material, and instead may be formed using other materials such as plastic, silicon rubber, etc. As another example, the exterior body 436 may be formed as or using a weaker magnet (or ferromagnetic or magnetic material having a weaker magnetic force) as compared to the ferromagnetic or magnetic material of the body 432 and/or the protruding portion 434. As another example, the exterior body 436 may be partially formed as or using one or more magnets and/or magnetic sections (or ferromagnetic or magnetic material) having a same, weaker, and/or stronger magnetic force as compared to the ferromagnetic or magnetic material of the body 432 and/or the protruding portion 434. It is recognized in the present disclosure that having the exterior body 436 not being magnetically coupled to the second magnetic implant assembly 430' (or being magnetically coupled to the second magnetic implant assembly 430' with a lesser magnetic force) results in a force or pressure (F1) exerted on a first portion of the cavity wall of the patient (i.e., force between the exterior body 436 and the second magnetic implant assembly 430') to be less than a force or pressure (F2) exerted on a second (adjacent) portion of the cavity wall of the patient (i.e., force between the protrusion 434 and the second magnetic implant assembly 430'). In this regard, it is recognized in the present disclosure that the adjacent application of different forces or pressures, as described above and in the present disclosure, improves the healing (and/or enables better controlled healing) of the anastomosis and/or necrosis formed by the first and second magnetic implant assemblies 430, 430'.

In example embodiments where the first magnetic implant assembly 430 includes a circular or ring-shaped protrusion 434 formed on the front wall 432a, the second magnetic implant assembly 430' may be formed as and/or include a flat and cylindrical body 432' (e.g., flat when viewed from the side and circular when viewed from the top).

The second magnetic implant assembly 430' includes a front wall 432a' (e.g., the upper wall 432a' of the lower magnetic implant assembly 430' illustrated in FIGS. 7A and 7B). In example embodiments, the front wall 432a' is the wall that will be magnetically coupled to or facing the second magnetic implant assembly 430'. The front wall 432a' may have a circular shape with a central axis formed through the center of the front wall 432a'. The front wall 432a' may have a radius equal or not equal to R1 (from the central axis), but larger than radius R2. In an example embodiment, the second magnetic implant assembly 430' may also include a hole, bore, or the like, through the center axis, similar to that of the first magnetic implant assembly 430.

The second magnetic implant assembly 430' includes a rear wall 432b' opposite to the front wall 432a'. In example embodiments, the rear wall 432b' is not the wall that will be magnetically coupled to or facing the first magnetic implant assembly 430. The rear wall 432b' will have substantially the same shape and central axis as the front wall 432a', and radius (from the central axis).

The second magnetic implant assembly 430' includes a second exterior circumferential sidewall 432c' formed around the magnetic body 432'. The second exterior circumferential sidewall 432c' may define a thickness of the magnetic body 432' and the protrusion 434. The thickness of the magnetic body 432' may or may not be the same as the thickness of the magnetic body 432 of the first magnetic implant assembly 430.

In an example embodiment, the front wall 432a' of the second magnetic implant assembly 430' does not include any protrusions like that of the first magnetic implant assembly 430. It is recognized in the present disclosure that not having protrusions on the front wall 432a' of the second magnetic implant assembly 430' allows for a simple and aligned magnetic coupling with the front wall 432a (i.e., with the protrusions 434) of the first magnetic implant assembly 430 (as illustrated in FIG. 7B). It is to be understood, however, that the front wall 432a' of the second magnetic implant assembly 430' may also include one or more protrusions (not shown) similar to (e.g., different exterior and/or interior radiuses) or the same as (e.g., same exterior and/or interior radiuses) the protrusions 434 of the front wall 432 of the first magnetic implant assembly 430.

It is to be noted in the present disclosure that the first magnetic implant assembly 430 (and/or the second magnetic implant assembly 430') may also include one or more indentations 435 on the front wall 432a (and 432a'). For example, the section 435 of the front wall 432a between the interior radius R3 and the central axis (or the radius R4 for the example embodiment illustrated in FIG. 6D) may be an indentation.

It is to be understood in the present disclosure that an exterior body (e.g., similar to the exterior body 436 described above for the first magnetic implant assembly 430) may be formed around and fixedly secured to the second exterior circumferential sidewall 432c' of the second magnetic implant assembly 430' in addition to or in replacement of the exterior body 436 for the first magnetic implant assembly 430 without departing from the teachings of the present disclosure.

The Securing Assembly (e.g., Securing Assembly 440).

As illustrated in at least FIGS. 2 and 5A-H, the second main body assembly 400 includes a securing assembly (e.g., securing assembly 440). The securing assembly 440 is configured to secure the magnetic implant assembly 430 to and unsecure the magnetic implant assembly 430 from the second main body 402.

The securing assembly 440 may be configured in one or more configurations. For example, as illustrated in FIGS. 5A-B and FIGS. 5E-F and as will be further described in the present disclosure, the securing assembly 440 may be configured in the form of a gripper 440, or the like. As another example, as illustrated in FIGS. 5C-D and as will be further described in the present disclosure, the securing assembly 440 may be configured in the form of a quarter or half rotation screw lock 440. As another example, as illustrated in FIGS. 5G-H and as will be further described in the present disclosure, the securing assembly 440 may be configured using a snare 440, or the like.

Example embodiments of the securing assembly 440 will now be described with reference to FIGS. 5A-H.

First Example Embodiment of the Securing Assembly 440

As illustrated in the perspective view of FIG. 5A and cross-sectional view of FIG. 5B, a securing assembly 440 may be formed as and/or include a gripper 440, or the like, for gripping at least a portion of the exterior circumferential sidewall 432c of the magnetic implant assembly 430. In an example embodiment, the magnetic implant assembly 430 may include a hole 430a for use in receiving a protruding portion 402a of the second main body 402. In example embodiments, the gripper 440 may be sized so as to grip more than half of the circumference or perimeter of the magnetic implant assembly 430.

In example embodiments, a wire or cable (not shown) may be secured at one end to a portion of the magnetic implant assembly 430 and provided through the hole 430a, second main body 402, and back to the controller (not shown) and/or surgeon console. Such a wire or cable may be useful in situations where the magnetic implant assembly 430 is accidentally, unintentionally, or mistakenly unsecured from the securing assembly 440. Such a wire or cable may be cut or disconnected at or close to the magnetic implant assembly 430 upon the magnetic implant assembly 430 being magnetically coupled to another magnetic implant assembly 430'.

Second Example Embodiment of the Securing Assembly 440

As illustrated in the perspective view of FIG. 5C and cross-sectional view of FIG. 5D, a securing assembly 440 may be formed as and/or include a screw lock 440, or the like, for securing and unsecuring the magnetic implant assembly 430. More specifically, the magnetic implant assembly 430 may include a quarter or half rotation (or other) threaded hole 430a for use in receiving a screw-like protruding portion 402a of the second main body 402.

As described above and in the present disclosure, a wire or cable (not shown) may be secured at one end to a portion of the magnetic implant assembly 430 and provided through the hole 430a, second main body 402, and back to the controller (not shown) and/or surgeon console (not shown).

Third Example Embodiment of the Securing Assembly 440

As illustrated in the perspective view of FIG. 5E and cross-sectional view of FIG. 5F, a securing assembly 440 may be formed as and/or include a gripper 440, or the like, for gripping at least a portion of the front wall 432*a* and rear wall 432*b* (and/or at least a portion of a protrusion (not shown) similar to the protrusions illustrated in FIGS. 6A-D and 7A-D) of the magnetic implant assembly 430. In an example embodiment, the magnetic implant assembly 430 may include a hole 430*a* for use in receiving a protruding portion 402*a* of the second main body 402.

As described above and in the present disclosure, a wire or cable (not shown) may be secured at one end to a portion of the magnetic implant assembly 430 and provided through the hole 430*a*, second main body 402, and back to the controller (not shown) and/or surgeon console.

Fourth and Fifth Example Embodiments of the Securing Assembly

As illustrated in the perspective view of FIG. 5G, the securing assembly may be formed as and/or include a snare, or the like, for securing and unsecuring the magnetic implant assembly 430. More specifically, the magnetic implant assembly 430 includes a first cable 442 secured at one end to an actuatable member 444 and provided through the system 100 to a second end (i.e., at the end where the controller (not shown) or surgeon console (not shown) is located). The magnetic implant assembly 430 also includes a second cable 446 secured at both ends to the actuatable member 444. The second cable 446 is fittedly provided in a groove, channel, or the like, formed around the exterior circumferential sidewall 432*c* of the magnetic implant assembly 430 so as to prevent the second cable 446 from sliding around relative to and/or coming away from the exterior circumferential sidewall 432*c*.

When the magnetic implant assembly 430 is to be secured to the second main body 402, the first cable 442 is persistently pulled at the second end in such a way that the actuatable member 444 is persistently held in a first (secured) position (i.e., a furthest position from the magnetic implant assembly 430 (or a furthest position from the most distal point of the second end of the second main body 402)). At the first (secured) position, the second cable 446 is persistently held in the groove of the exterior circumferential sidewall 432*c*, and the magnetic implant assembly 430 is accordingly secured to the second main body 402.

When the magnetic implant assembly 430 is to be unsecured from the second main body 402 (e.g., when the magnetic implant assembly 430 is to be magnetically coupled to another magnetic implant assembly 430'), the first cable 442 is released or pushed from the second end in such a way that the actuatable member 444 is moved to a second (unsecured) position (i.e., a position that is closer to the magnetic implant assembly 430 (or a position that is closer to the most distal point of the second end of the second main body 402)). At the second (unsecured) position, the second cable 446 is no longer persistently held in the groove of the exterior circumferential sidewall 432*c* (i.e., becomes looser, becomes a bigger loop), and the magnetic implant assembly 430 is accordingly unsecured or unsecurable from the second main body 402.

The securing assembly may be formed as and/or include other configurations of a snare, or the like, for securing and unsecuring the magnetic implant assembly 430. For example, as illustrated in FIG. 5H, the magnetic implant assembly 430 includes a first cable 442 secured at one end to an actuatable member 444, provided in a groove, channel, or the like, formed around the exterior circumferential sidewall 432*c* of the magnetic implant assembly 430, provided through the second main body 402, and provided through the rest of the system 100 to a second end (i.e., at the end where the controller (not shown) or surgeon console (not shown) is located). The first cable 442 is fittedly provided in the groove formed around the exterior circumferential sidewall 432*c* of the magnetic implant assembly 430 so as to prevent the second cable 446 from sliding around relative to and/or coming away from the exterior circumferential sidewall 432*c*.

When the magnetic implant assembly 430 is to be secured to the second main body 402, the first cable 442 is persistently pulled at the second end in such a way that the magnetic implant assembly 430 is persistently secured by the first cable 442.

When the magnetic implant assembly 430 is to be unsecured from the second main body 402 (e.g., when the magnetic implant assembly 430 is to be magnetically coupled to another magnetic implant assembly 430'), the first cable 442 is released or pushed from the second end in such a way that the first cable 442 is no longer persistently held in the groove of the exterior circumferential sidewall 432*c* (i.e., becomes looser, becomes a bigger loop), and the magnetic implant assembly 430 is accordingly unsecured or unsecurable from the second main body 402.

Other embodiments and/or configurations of snares are also contemplated in the present disclosure.

As described above and in the present disclosure, a wire or cable (not shown) may be secured at one end to a portion of the magnetic implant assembly 430 and provided through the hole 430*a*, second main body 402, and back to the controller (not shown) and/or surgeon console.

Example Embodiments of a Method of Delivering a Magnetic Implant Assembly Rectally FIGS. 8A-8Q illustrate an example embodiment of a method of delivering a magnetic implant assembly. The magnetic implant assembly may be or include one or more example embodiments of the magnetic implant assembly 430 (or second magnetic implant assembly 430') described in the present disclosure. The method may be performed using one or more example embodiments of the endoscopic anastomosis system 100 described in the present disclosure, which includes the first main body assembly 200, the head assembly 300, the second main body assembly 400, and a first magnetic implant assembly 430. The method illustrated in FIGS. 8A-8Q is an example embodiment of a method of delivering a magnetic implant assembly rectally (i.e., via the rectum and anus).

As illustrated in FIG. 8A and FIG. 8B, an example embodiment of the method includes inserting the system 100 (which includes example embodiments of the first main body assembly 200, the head assembly 300, and the second main body assembly 400, as described in the present disclosure) in the anus and through the rectum.

As illustrated in FIG. 8C and FIG. 8D, an example embodiment of the method includes bending or turning the system 100 (e.g., via the first bendable section 210 of the first main body assembly 200) and further advancing the system 100 around one or more bends or turns and into the sigmoid colon.

As illustrated in FIG. 8E, once the head assembly 300 is advanced around the bend or turn, the head assembly 300 (and first main body assembly 200) is anchored or secured to a portion of the cavity wall of the patient (e.g., by controlling/configuring the first expandable member 320 to expand radially outwards while also controlling/configuring the first pressure port (not shown here, but as described for first pressure port 332) to provide a negative pressure to encourage, bring in, suction inward, and/or collapse a portion of cavity wall of the patient towards the head assembly 300).

As illustrated in FIG. 8F, once the cavity wall of the patient is anchored or secured to the head assembly 300 and the first main body assembly 200 (as described above for FIG. 8E), the bend or turn in the colon may be straightened by pulling the system 100 (i.e., pulling the first main body assembly 200) back so as to concertina the colon.

As illustrated in FIG. 8G, once the colon has been straightened, the system 100 can be unanchored or unsecured from the cavity wall of the colon (e.g., by unexpanding or deflating the first expandable member 320 and not applying negative pressure (or applying positive pressure) by the first pressure port).

As illustrated in FIG. 8H and FIG. 8I, an example embodiment of the method includes advancing the system 100 through the descending colon, splenic flexure, transverse colon, hepatic flexure, and ascending colon until the head assembly 300 approaches the ileocecal valve.

As illustrated in FIG. 8J, FIG. 8K, and FIG. 8L, an example embodiment of the method includes bending or turning the system 100 (e.g., via the first bendable section 210 of the first main body assembly 200) and further advancing the system 100 into and through the ileocecal valve.

As illustrated in FIG. 8M, once the head assembly 300 is advanced into the ileocecal valve and to the small bowel, the head assembly 300 (and first main body assembly 200) is anchored or secured to a portion of the cavity wall (e.g., by controlling/configuring the first expandable member 320 to expand radially outwards while also controlling/configuring the first pressure port (not shown here, but as described for first pressure port 332) to provide a negative pressure to encourage, bring in, suction inward, and/or collapse a portion of cavity wall of the patient towards the head assembly 300).

As illustrated in FIG. 8N, once the cavity wall of the patient is anchored or secured to the head assembly 300 and first main body assembly 200 (as described above for FIG. 8M), the second main body assembly 400 (which includes example embodiments of the second main body 402, the second expandable member 420, and the magnetic implant assembly 430, as described in the present disclosure) is advanced forward by sliding the second main body assembly 400 forward relative to the anchored first main body assembly 200.

As illustrated in FIG. 8O, after the second main body assembly 400 has been advanced forward, the second main body assembly 400 may be anchored or secured to a portion of the cavity wall (e.g., by controlling/configuring the second expandable member 420 to expand radially outwards while also controlling/configuring the second pressure port (not shown here, but as described for second pressure port 442) to provide a negative pressure to encourage, bring in, suction inward, and/or collapse a portion of cavity wall of the patient towards the second main body 402).

As illustrated in FIG. 8P, once the cavity wall of the patient is anchored or secured to the second main body assembly 400 (as described above for FIG. 8O), the head assembly 300 and first main body assembly 200 may be unanchored or unsecured (e.g., by unexpanding or deflating the first expandable member 320 and not applying negative pressure (or applying positive pressure) by the first pressure port).

As illustrated in FIG. 8Q, after the head assembly 300 and the first main body assembly 200 have been unanchored or unsecured (as described above for FIG. 8P), the first main body assembly 200 and head assembly 300 are advanced forward toward the second expandable member 420 of the second main body assembly 400.

As illustrated in FIG. 8R, the head assembly 300 and first main body assembly 200 are then anchored or secured to a portion of the cavity wall of the patient (e.g., by controlling/configuring the first expandable member 320 to expand radially outwards while also controlling/configuring the first pressure port to provide a negative pressure to encourage, bring in, suction inward, and/or collapse a portion of cavity wall of the patient towards the head assembly 300). As explained for FIG. 8N, the second main body assembly 400 is then advanced forward.

As illustrated in FIG. 8S, the steps illustrated in FIGS. 8N-8R are repeated as necessary until the head assembly 300 approaches a distance of about 20-30 cm from the ileocecal valve. At this point, the system 100 is ready to deliver the magnetic implant assembly 430 to magnetically couple with another magnetic implant assembly 430' delivered orally (i.e., via the mouth).

Example Embodiments of a Method of Delivering a Magnetic Implant Assembly Orally FIGS. 9A-9I illustrate another example embodiment of a method of delivering a magnetic implant assembly. The magnetic implant assembly may be or include one or more example embodiments of the magnetic implant assembly 430' (or 430) described in the present disclosure. The method may be performed using one or more example embodiments of the endoscopic anastomosis system 100 described in the present disclosure, which includes the first main body assembly 200, the head assembly 300, the second main body assembly 400, and a second magnetic implant assembly 430'. The method illustrated in FIGS. 9A-9I is an example embodiment of a method of delivering a magnetic implant assembly orally (i.e., via the mouth and esophagus).

Figures 9A, 9B:
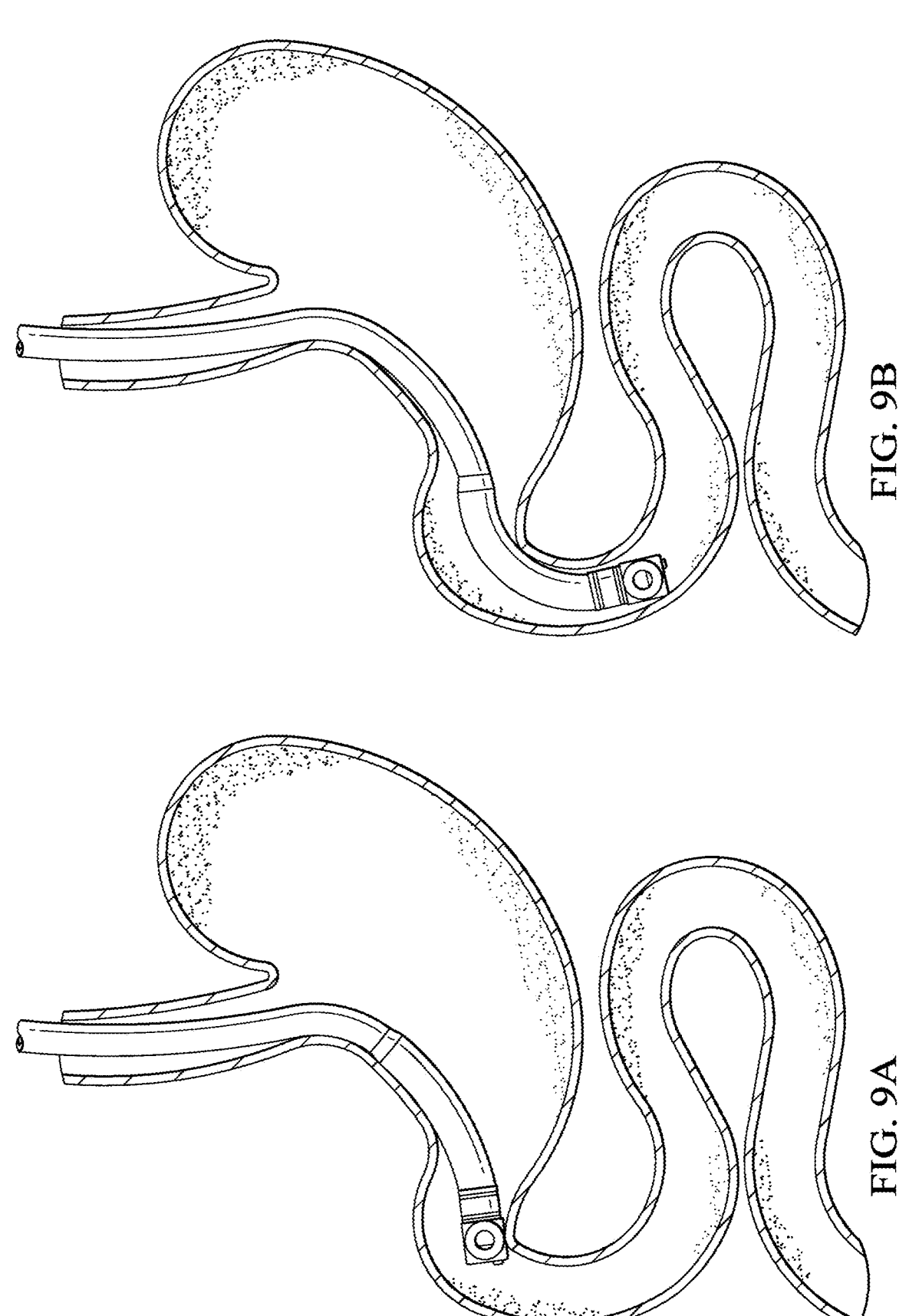

As illustrated in FIG. 9A and FIG. 9B, an example embodiment of the method includes inserting the system 100 (which includes example embodiments of the first main body assembly 200, the head assembly 300, and the second main body assembly 400, as described in the present disclosure) in the mouth, through the esophagus, and through the stomach. Once the system 100 has reached the pyloric sphincter, the system 100 is configured to bend or turn (e.g., via the first bendable section 210 of the first main body assembly 200) into the pyloric sphincter.

Figures 9C, 9D:
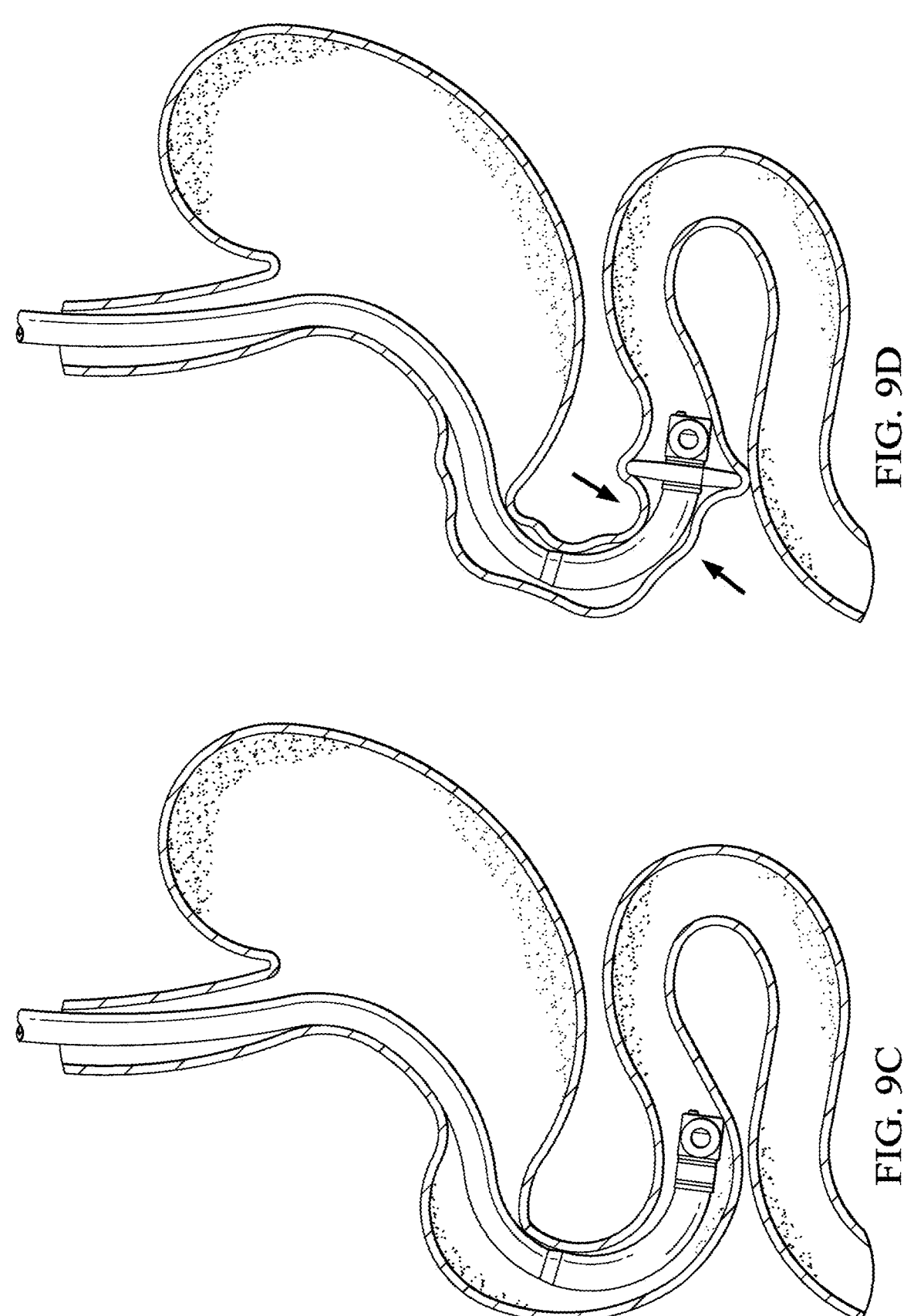

As illustrated in FIG. 9C, an example embodiment of the method includes further advancing the system 100 to the duodenum.

As illustrated in FIG. 9D, once the head assembly 300 is advanced forward, the system 100 is anchored or secured to a portion of the cavity wall of the patient (e.g., by controlling/configuring the first expandable member 320 to expand radially outwards while also controlling/configuring the first pressure port (not shown here, but as described for first pressure port 332) to provide a negative pressure to encourage, bring in, suction inward, and/or collapse a portion of cavity wall of the patient towards the head assembly 300).

Figures 9E, 9F:
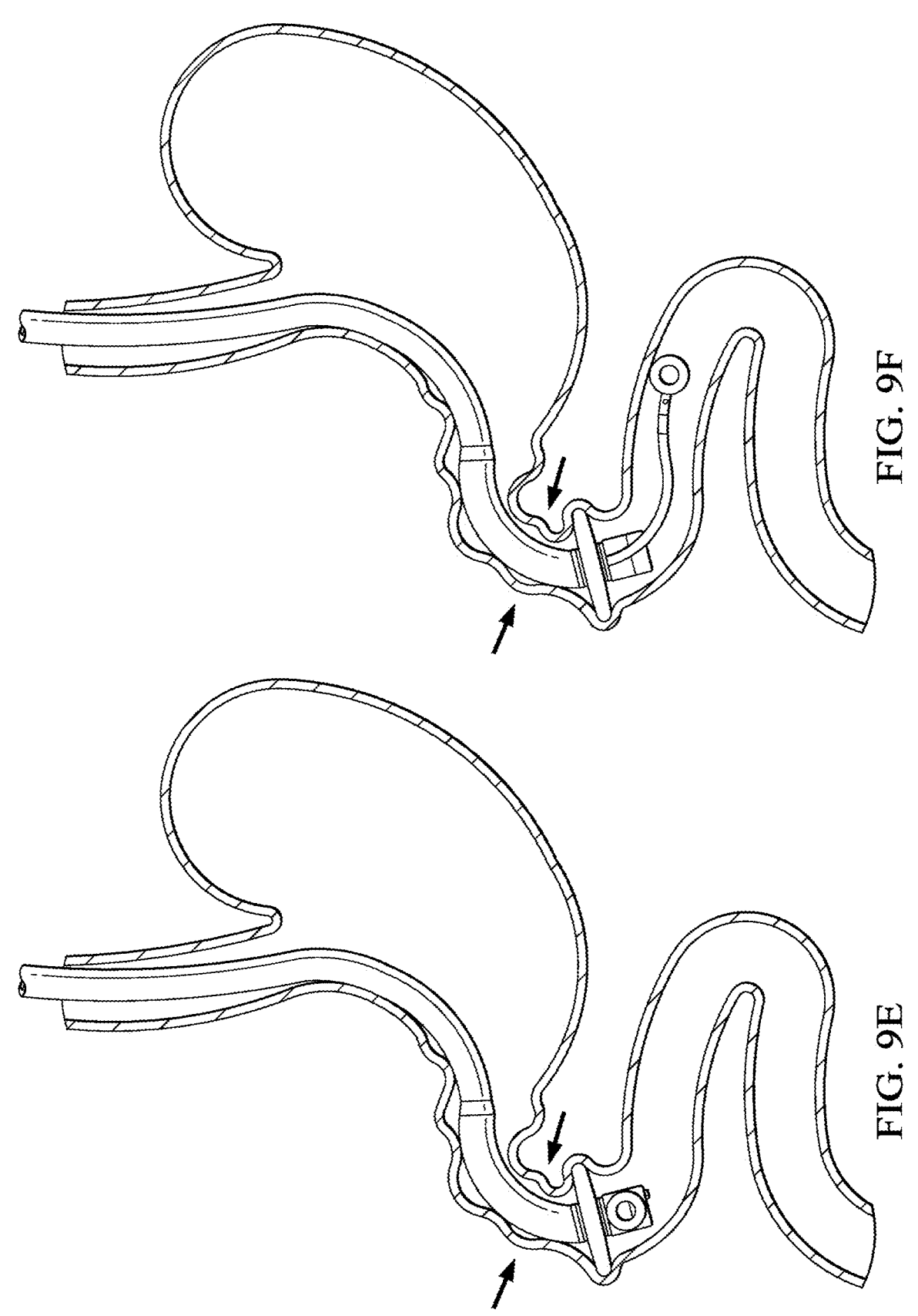

As illustrated in FIG. 9E, once the cavity wall of the patient is anchored or secured to the system 100 (as described above for FIG. 9D), the bend or turn may be straightened by pulling the system 100 (i.e., pulling the first main body assembly 200) back so as to concertina the duodenum.

As illustrated in FIG. 9F, the second main body assembly 400 (which includes example embodiments of the second main body 402, the second expandable member 420, and the magnetic implant assembly 430, as described in the present disclosure) is advanced forward by sliding the second main body assembly 400 forward relative to the anchored first main body assembly 200.

Figures 9G, 9H:
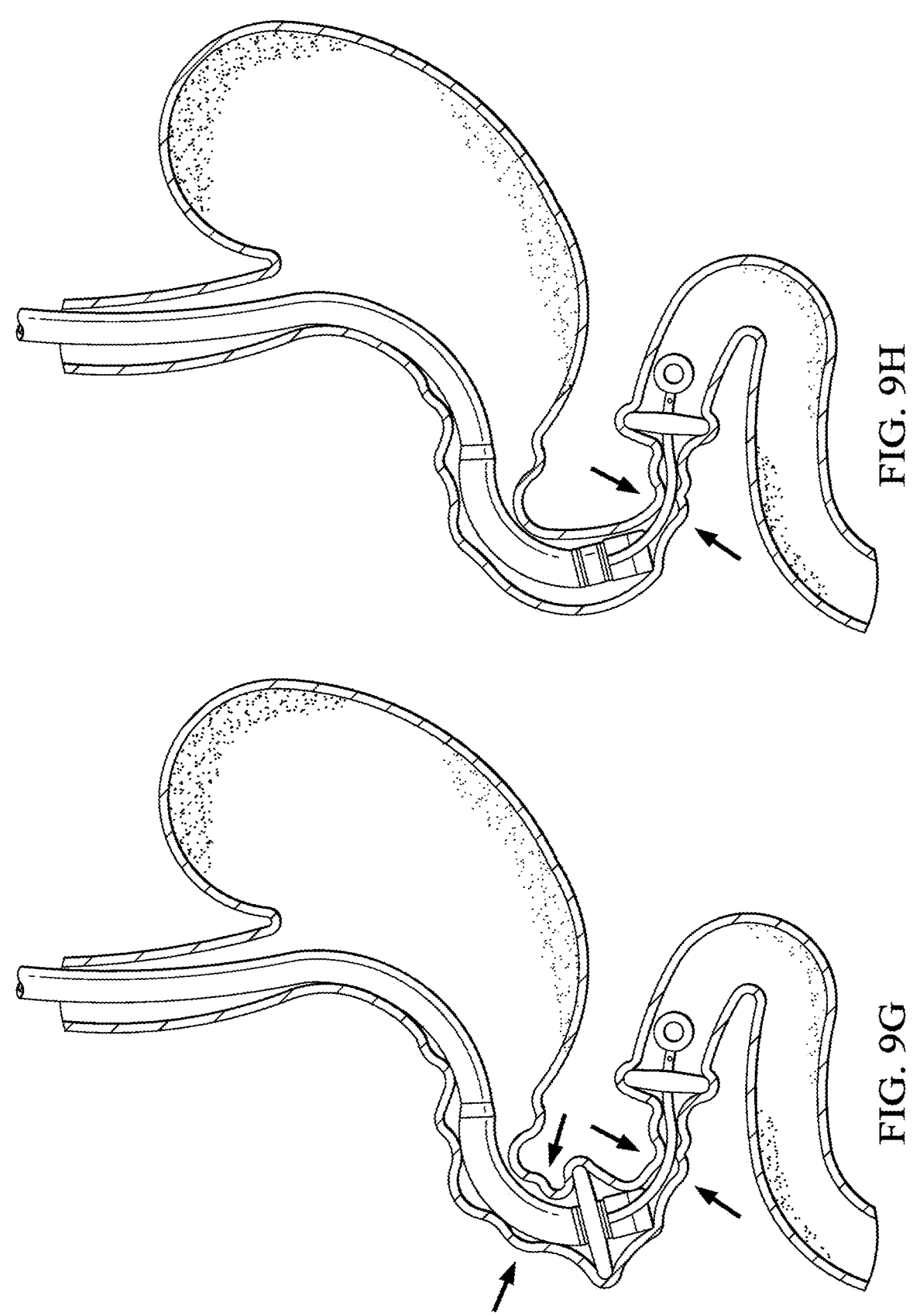

As illustrated in FIG. 9G, after the second main body assembly 400 has been advanced forward, the second main body assembly 400 may be anchored or secured to a portion of the cavity wall (e.g., by controlling/configuring the second expandable member 420 to expand radially outwards while also controlling/configuring the second pressure port (not shown here, but as described for second pressure port 442) to provide a negative pressure to encourage, bring in, suction inward, and/or collapse a portion of cavity wall of the patient towards the second main body 402).

As illustrated in FIG. 9H, once the cavity wall of the patient is anchored or secured to the second main body assembly 400 (as described above for FIG. 9G), the head assembly 300 and first main body assembly 200 may be unanchored or unsecured (e.g., by unexpanding or deflating the first expandable member 320 and not applying negative pressure (or applying positive pressure) by the first pressure port).

Figure 9I:
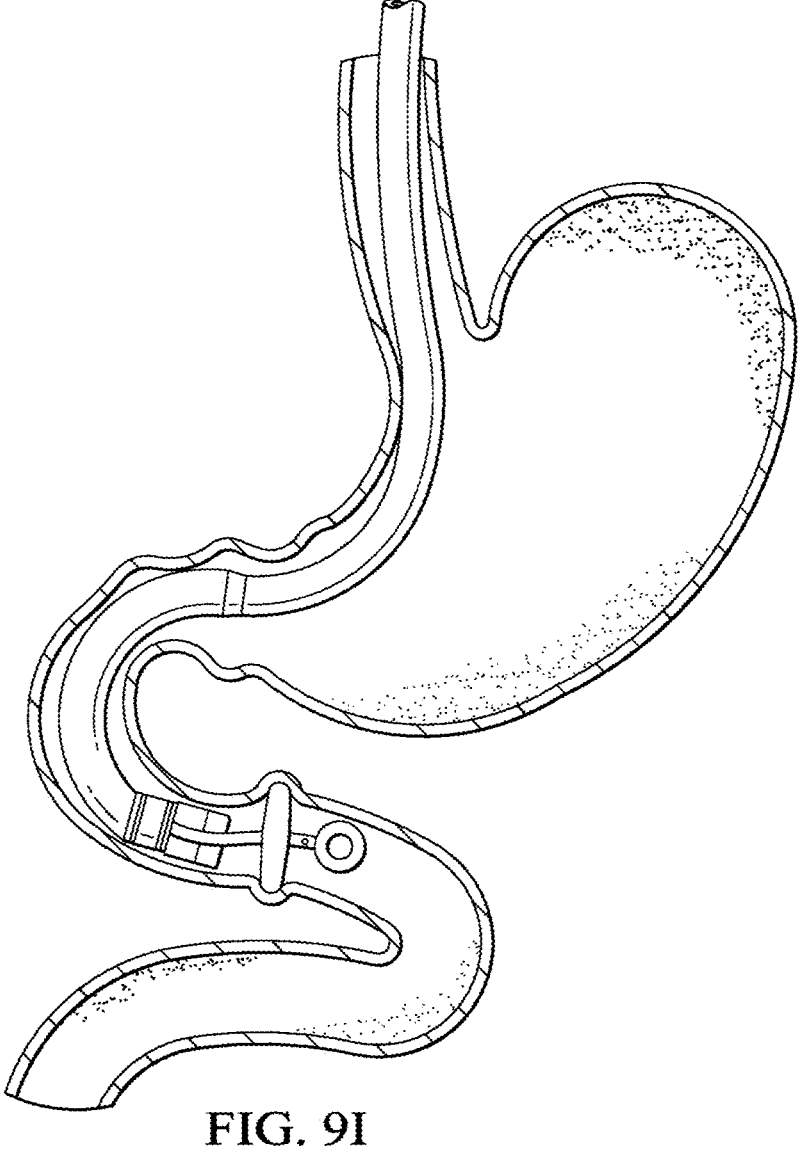

As illustrated in FIG. 9I, after the head assembly 300 and the first main body assembly 200 have been unanchored or unsecured (as described above for FIG. 8P), the first main body assembly 200 and head assembly 300 are advanced forward toward the second expandable member 420 of the second main body assembly 400. The steps illustrated in FIGS. 9D-9I are repeated as necessary until the head assembly 300 approaches the target location/position in the distal duodenum/jejunum (i.e., the location where the first magnetic implant assembly 430 has been delivered, as described in FIGS. 8A-S). The method then includes delivering the second magnetic implant assembly 430' to magnetically couple with magnetic implant assembly 430 delivered rectally (as described in FIGS. 8A-S).

While various embodiments in accordance with the disclosed principles have been described above, it should be understood that they have been presented by way of example only, and are not limiting. Thus, the breadth and scope of the example embodiments described in the present disclosure should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

For example, "assembly," "device," "portion," "segment," "member," "body," or other similar terms should generally be construed broadly to include one part or more than one part attached or connected together.

Various terms used herein have special meanings within the present technical field. Whether a particular term should be construed as such a "term of art" depends on the context in which that term is used. "Connected," "connecting," "attached," "attaching," "anchored," "anchoring," "in communication with," "communicating with," "associated with," "associating with," or other similar terms should generally be construed broadly to include situations where attachments, connections, and anchoring are direct between referenced elements or through one or more intermediaries between the referenced elements. These and other terms are to be construed in light of the context in which they are used in the present disclosure and as one of ordinary skill in the art would understand those terms in the disclosed context. The above definitions are not exclusive of other meanings that might be imparted to those terms based on the disclosed context.

As referred to in the present disclosure, a computing device, controller, manipulator, master input device, a processor, and/or a system may be a virtual machine, computer, node, instance, host, and/or device in a networked or non-networked computing environment. A networked computing environment may be a collection of devices connected by communication channels that facilitate communications between devices and allow devices to share resources. Also as referred to in the present disclosure, a computing device may be a device deployed to execute a program operating as a socket listener and may include software instances.

Resources may encompass any type of resource for running instances including hardware (such as servers, clients, mainframe computers, networks, network storage, data sources, memory, central processing unit time, scientific instruments, and other computing devices), as well as software, software licenses, available network services, and other non-hardware resources, or a combination thereof.

A networked computing environment may include, but is not limited to, computing grid systems, distributed computing environments, cloud computing environment, etc. Such networked computing environments include hardware and software infrastructures configured to form a virtual organization comprised of multiple resources that may be in geographically disperse locations.

Furthermore, the coverage of the present application and any patents issuing from the present application may extend to one or more communications protocols, including TCP/IP.

Words of comparison, measurement, and timing such as "at the time," "equivalent," "during," "complete," and the like should be understood to mean "substantially at the time," "substantially equivalent," "substantially during," "substantially complete," etc., where "substantially" means that such comparisons, measurements, and timings are practicable to accomplish the implicitly or expressly stated desired result.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, a description of a technology in the "Background" is not to be construed as an admission that technology is prior art to any invention(s) in this disclosure. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention (s), and their equivalents, that are protected thereby. In all instances, the scope of such claims shall be considered on their own merits in light of this disclosure, but should not be constrained by the headings herein.

What is claimed is:

1. An endoscopic anastomosis system, the endoscopic anastomosis system comprising:

a first main body assembly, the first main body assembly being an elongated body having a first end and a second end, at least a portion of the second end of the first main body assembly controllable to bend in a plurality of directions;

a head assembly, the head assembly having a first end and a second end, the first end of the head assembly secured to the second end of the first main body assembly, the head assembly including:

a head assembly body, the head assembly body including:

a second main body assembly opening;

a first pressure port, the first pressure port configured to apply a negative pressure; and a first expandable member, the first expandable member secured to at least a portion of the head assembly body, the first expandable member configured to expand radially away from the head assembly body;

a second main body assembly, the second main body assembly being an elongated body having a first end and a second end, at least a portion of the second end of the second main body assembly provided in and moveable through the second main body assembly opening of the head assembly body, the second main body assembly including:

a second expandable member, the second expandable member secured to a portion of the second end of the second main body assembly, the second expandable member configured to expand radially away from the second main body assembly; and a second pressure port, the second pressure port configured to apply a negative pressure; and a magnetic implant assembly, the magnetic implant assembly securable to and unsecurable from the second end of the second main body assembly, the magnetic implant assembly including:

a magnetic body, the magnetic body formed as a cylindrical body with a central axis, the magnetic body including:

a front wall;

a rear wall opposite to the front wall; and an exterior circumferential sidewall formed around the magnetic body, the exterior circumferential sidewall defining a thickness of the magnetic body, the exterior circumferential sidewall formed at a first radius from the central axis.

2. The endoscopic anastomosis system of claim 1, further comprising a securing assembly, the securing assembly secured to the second end of the second main body assembly, the securing assembly actuatable between a locked configuration and an unlocked configuration, the locked configuration being a configuration in which the magnetic implant assembly is secured to the securing assembly, the unlocked configuration being a configuration in which the magnetic implant assembly is not secured to the securing assembly.

3. The endoscopic anastomosis system of claim 2, wherein one or more of the following apply:

at least a portion of the second end of the second main body assembly is configured to bend in a plurality of directions; and/or the second expandable member, the second pressure port, and the securing assembly are arranged in such a way that the second pressure port is provided between the second expandable member and the securing assembly; and/or at least a portion of the second end of the second main body assembly is configured to rotate relative to a central axis, the central axis being an axis formed by the at least one portion of the second end of the second main body assembly; and/or the magnetic body includes a hole formed through the magnetic body between the front wall and the rear wall; and/or the front wall of the magnetic body includes a circular shaped indentation centrally aligned with the central axis, the circular shaped indentation having a first exterior radius from the central axis, the first exterior radius of the circular shaped indentation being less than the first radius; and/or wherein the head assembly body further includes an image capturing assembly; and/or wherein the head assembly body further includes an insufflation port, the insufflation port configured to apply a positive pressure.

4. The endoscopic anastomosis system of claim 1, wherein the magnetic implant assembly further includes:

one or more protruding portions, the one or more protruding portions formed on the front wall of the magnetic body.

5. The endoscopic anastomosis system of claim 4, wherein the one or more protruding portions include a first ring shaped protrusion formed on the front wall of the magnetic body, the first ring shaped protrusion centrally aligned with the central axis, the first ring shaped protrusion having a first exterior radius from the central axis and a first interior radius from the central axis, the first exterior radius of the first ring shaped protrusion being equal to or less than the first radius.

6. The endoscopic anastomosis system of claim 5, wherein the first exterior radius of the first ring shaped protrusion is less than the first radius.

7. The endoscopic anastomosis system of claim 5, wherein the first exterior radius of the first ring shaped protrusion is equal to the first radius; and wherein the magnetic implant assembly further includes an exterior ring shaped body, the exterior ring shaped body formed around and fixedly secured to the exterior circumferential sidewall of the magnetic body, at least a portion of the exterior ring shaped body adjacent to the front wall of the magnetic body, wherein at least a portion of the exterior ring shaped body is formed using a material other than a ferromagnetic or magnetic material.

8. The endoscopic anastomosis system of claim 5, wherein the one or more protruding portions further includes a second ring shaped protrusion formed on the first ring shaped protrusion, the second ring shaped protrusion centrally aligned with the central axis and the first ring shaped protrusion, the second ring shaped protrusion having a second exterior radius from the central axis and a second interior radius from the central axis, the second exterior radius of the second ring shaped protrusion being less than the first exterior radius.

9. The endoscopic anastomosis system of claim 1, wherein the front wall of the magnetic body includes a ring shaped indentation centrally aligned with the central axis, the ring shaped indentation having a first exterior radius from the central axis and a second exterior radius from the central axis, the first exterior radius of the ring shaped indentation being equal to the first radius, the second exterior radius of the ring shaped indentation being less than the first radius; and wherein the magnetic implant assembly further includes an exterior ring shaped body, the exterior ring shaped body formed around and fixedly secured to the exterior circumferential sidewall of the magnetic body, at least a portion of the exterior ring shaped body adjacent to the front wall of the magnetic body, wherein at least a portion of the exterior ring shaped body is formed using a material other than a ferromagnetic or magnetic material.

10. An endoscopic anastomosis system, the endoscopic anastomosis system comprising:

a first main body assembly, the first main body assembly being an elongated body having a first end and a second end, at least a portion of the second end of the first main body assembly controllable to bend in a plurality of directions;

a head assembly, the head assembly having a first end and a second end, the head assembly including:

a head assembly body, the head assembly body including:

a first region, the first region having a first end, a second end, and a midsection between the first and second ends of the first region, the first end of the first region secured to the second end of the first main body assembly, the second end of the first region including:

a first section, the first section secured to a first end of a second region of the head assembly; and a second section, the second section having a second main body assembly opening; and the second region, the second region having the first end and a second end, the second end of the second region including:

a first pressure port, the first pressure port configured to apply a negative pressure; and a first expandable member, the first expandable member secured to at least a portion of the midsection of the first region of the head assembly body, the first expandable member configured to expand radially away from the first region of the head assembly body;

a second main body assembly, the second main body assembly being an elongated body having a first end and a second end, at least a portion of the second end of the second main body assembly provided in and moveable through the second main body assembly opening of the second section of the first region of the head assembly body, the second main body assembly including:

a second expandable member, the second expandable member secured to a portion of the second end of the second main body assembly, the second expandable member configured to expand radially away from the second main body assembly; and a second pressure port, the second pressure port configured to apply a negative pressure;

a magnetic implant assembly, the magnetic implant assembly including:

a magnetic body, the magnetic body formed as a cylindrical body with a central axis, the magnetic body including:

a front wall;

a rear wall opposite to the front wall; and an exterior circumferential sidewall formed around the magnetic body, the exterior circumferential sidewall defining a thickness of the magnetic body, the exterior circumferential sidewall formed at a first radius from the central axis; and a securing assembly, the securing assembly secured to the second end of the second main body assembly, the securing assembly actuatable between a locked configuration and an unlocked configuration, the locked configuration being a configuration in which the magnetic implant assembly is secured to the securing assembly, the unlocked configuration being a configuration in which the magnetic implant assembly is not secured to the securing assembly.

11. The endoscopic anastomosis system of claim 10, wherein at least one of the following apply:

the second region of the head assembly body further includes an image capturing assembly; and/or the second region of the head assembly body further includes an insufflation port, the insufflation port configured to apply a positive pressure; and/or the first region of the head assembly body is cylindrical in shape; and/or the second region of the head assembly body is semi-cylindrical in shape; and/or the first and second sections of the first region of the head assembly body are semi-circular in shape; and/or at least a portion of the second end of the second main body assembly is configured to bend in a plurality of directions; and/or the second expandable member, the second pressure port, and the securing assembly are arranged in such a way that the second pressure port is provided between the second expandable member and the securing assembly; and/or at least a portion of the second end of the second main body assembly is configured to rotate relative to a central axis, the central axis being an axis formed by the at least one portion of the second end of the second main body assembly; and/or the magnetic body includes a hole formed through the magnetic body between the front wall and the rear wall; and/or the front wall of the magnetic body includes a circular shaped indentation centrally aligned with the central axis, the circular shaped indentation having a first exterior radius from the central axis, the first exterior radius of the circular shaped indentation being less than the first radius.

12. The endoscopic anastomosis system of claim 10, wherein the magnetic implant assembly further includes:

one or more protruding portions, the one or more protruding portions formed on the front wall of the magnetic body.

13. The endoscopic anastomosis system of claim 12, wherein the one or more protruding portions include a first ring shaped protrusion formed on the front wall of the magnetic body, the first ring shaped protrusion centrally aligned with the central axis, the first ring shaped protrusion having a first exterior radius from the central axis and a first interior radius from the central axis, the first exterior radius of the first ring shaped protrusion being equal to or less than the first radius.

14. The endoscopic anastomosis system of claim 13, wherein the first exterior radius of the first ring shaped protrusion is less than the first radius.

15. The endoscopic anastomosis system of claim 13, wherein the first exterior radius of the first ring shaped protrusion is equal to the first radius; and wherein the magnetic implant assembly further includes an exterior ring shaped body, the exterior ring shaped body formed around and fixedly secured to the exterior circumferential sidewall of the magnetic body, at least a portion of the exterior ring shaped body adjacent to the front wall of the magnetic body, wherein at least a portion of the exterior ring shaped body is formed using a material other than a ferromagnetic or magnetic material.

16. The endoscopic anastomosis system of claim 13, wherein the one or more protruding portions further includes a second ring shaped protrusion formed on the first ring shaped protrusion, the second ring shaped protrusion centrally aligned with the central axis and the first ring shaped protrusion, the second ring shaped protrusion having a second exterior radius from the central axis and a second interior radius from the central axis, the second exterior radius of the second ring shaped protrusion being less than the first exterior radius.

17. The endoscopic anastomosis system of claim 10, wherein the front wall of the magnetic body includes a ring shaped indentation centrally aligned with the central axis, the ring shaped indentation having a first exterior radius from the central axis and a second exterior radius from the central axis, the first exterior radius of the ring shaped indentation being equal to the first radius, the second exterior radius of the ring shaped indentation being less than the first radius; and wherein the magnetic implant assembly further includes an exterior ring shaped body, the exterior ring shaped body formed around and fixedly secured to the exterior circumferential sidewall of the magnetic body, at least a portion of the exterior ring shaped body adjacent to the front wall of the magnetic body, wherein at least a portion of the exterior ring shaped body is formed using a material other than a ferromagnetic or magnetic material.

18. An endoscopic anastomosis system, the endoscopic anastomosis system comprising:

a first main body assembly, the first main body assembly being an elongated body having a first end and a second end, at least a portion of the second end of the first main body assembly controllable to bend in a plurality of directions;

a head assembly, the head assembly having a first end and a second end, the head assembly including:

a head assembly body, the head assembly body including:

a first region, the first region having a first end, a second end, and a midsection between the first and second ends of the first region, the first end of the first region secured to the second end of the first main body assembly, the second end of the first region including:

a first section, the first section secured to a first end of a second region of the head assembly; and a second section, the second section having a second main body assembly opening; and the second region, the second region having the first end and a second end, the second end of the second region including:

a first pressure port, the first pressure port configured to apply a negative pressure; and a first expandable member, the first expandable member secured to at least a portion of the midsection of the first region of the head assembly body, the first expandable member configured to expand radially away from the first region of the head assembly body;

a second main body assembly, the second main body assembly being an elongated body having a first end and a second end, at least a portion of the second end of the second main body assembly provided in and moveable through the second main body assembly opening of the second section of the first region of the head assembly body, the second main body assembly including:

a second expandable member, the second expandable member secured to a portion of the second end of the second main body assembly, the second expandable member configured to expand radially away from the second main body assembly; and a second pressure port, the second pressure port configured to apply a negative pressure; and a securing assembly, the securing assembly secured to the second end of the second main body assembly, the securing assembly including a snare subassembly, the snare subassembly actuatable between a locked configuration and an unlocked configuration, the locked configuration being a configuration in which a cable loop formed by the snare subassembly is less than or equal to a first length, the unlocked configuration being a configuration in which a cable loop formed by the snare subassembly is greater than a first length.

19. The endoscopic anastomosis system of claim 18, further comprising:

a magnetic implant assembly, the magnetic implant assembly configured to be secured to the securing assembly when the cable loop of the snare subassembly is provided around the magnetic implant assembly and the snare subassembly is actuated to the locked configuration, the magnetic implant assembly configured to be unsecured to the securing assembly when the snare subassembly is actuated to the unlocked configuration.

20. The endoscopic anastomosis system of claim 19, wherein the magnetic implant assembly includes:

a magnetic body, the magnetic body formed as a cylindrical body with a central axis, the magnetic body including:

a front wall;

a rear wall opposite to the front wall; and an exterior circumferential sidewall formed around the magnetic body, the exterior circumferential sidewall defining a thickness of the magnetic body, the exterior circumferential sidewall formed at a first radius from the central axis.

21. The endoscopic anastomosis system of claim 18, wherein at least one of the following apply:

the second region of the head assembly body further includes an image capturing assembly; and/or the second region of the head assembly body further includes an insufflation port, the insufflation port configured to apply a positive pressure; and/or the first region of the head assembly body is cylindrical in shape; and/or the second region of the head assembly body is semi-cylindrical in shape; and/or the first and second sections of the first region of the head assembly body are semi-circular in shape; and/or at least a portion of the second end of the second main body assembly is configured to bend in a plurality of directions; and/or the second expandable member, the second pressure port, and the securing assembly are arranged in such a way that the second pressure port is provided between the second expandable member and the securing assembly; and/or at least a portion of the second end of the second main body assembly is configured to rotate relative to a central axis, the central axis being an axis formed by the at least one portion of the second end of the second main body assembly.

22. The endoscopic anastomosis system of claim 20, wherein:

the magnetic body includes a hole formed through the magnetic body between the front wall and the rear wall.

23. The endoscopic anastomosis system of claim 20, wherein the magnetic implant assembly further includes:

one or more protruding portions, the one or more protruding portions formed on the front wall of the magnetic body.

24. The endoscopic anastomosis system of claim 23, wherein the one or more protruding portions include a first ring shaped protrusion formed on the front wall of the magnetic body, the first ring shaped protrusion centrally aligned with the central axis, the first ring shaped protrusion having a first exterior radius from the central axis and a first interior radius from the central axis, the first exterior radius of the first ring shaped protrusion being equal to or less than the first radius.

25. The endoscopic anastomosis system of claim 24, wherein the first exterior radius of the first ring shaped protrusion is less than the first radius.

26. The endoscopic anastomosis system of claim 24, wherein the first exterior radius of the first ring shaped protrusion is equal to the first radius; and wherein the magnetic implant assembly further includes an exterior ring shaped body, the exterior ring shaped body formed around and fixedly secured to the exterior circumferential sidewall of the magnetic body, at least a portion of the exterior ring shaped body adjacent to the front wall of the magnetic body, wherein at least a portion of the exterior ring shaped body is formed using a material other than a ferromagnetic or magnetic material.

27. The endoscopic anastomosis system of claim 24, wherein the one or more protruding portions further includes a second ring shaped protrusion formed on the first ring shaped protrusion, the second ring shaped protrusion centrally aligned with the central axis and the first ring shaped protrusion, the second ring shaped protrusion having a second exterior radius from the central axis and a second interior radius from the central axis, the second exterior radius of the second ring shaped protrusion being less than the first exterior radius.

28. The endoscopic anastomosis system of claim 20, wherein the front wall of the magnetic body includes a circular shaped indentation centrally aligned with the central axis, the circular shaped indentation having a first exterior radius from the central axis, the first exterior radius of the circular shaped indentation being less than the first radius.

29. The endoscopic anastomosis system of claim 20, wherein the front wall of the magnetic body includes a ring shaped indentation centrally aligned with the central axis, the ring shaped indentation having a first exterior radius from the central axis and a second exterior radius from the central axis, the first exterior radius of the ring shaped indentation being equal to the first radius, the second exterior radius of the ring shaped indentation being less than the first radius; and wherein the magnetic implant assembly further includes an exterior ring shaped body, the exterior ring shaped body formed around and fixedly secured to the exterior circumferential sidewall of the magnetic body, at least a portion of the exterior ring shaped body adjacent to the front wall of the magnetic body, wherein at least a portion of the exterior ring shaped body is formed using a material other than a ferromagnetic or magnetic material.

* * * * *